(12) United States Patent
LiPuma et al.

(10) Patent No.: US 10,400,291 B2
(45) Date of Patent: Sep. 3, 2019

(54) METHOD FOR BACTERIAL SPECIES IDENTIFICATION AND STRAIN TYPING

(71) Applicant: The Regents of the University of Michigan, Ann Arbor, MI (US)

(72) Inventors: John LiPuma, Ann Arbor, MI (US); Theodore Spilker, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/752,391

(22) Filed: Jun. 26, 2015

(65) Prior Publication Data

US 2015/0376685 A1   Dec. 31, 2015

Related U.S. Application Data

(60) Provisional application No. 62/018,211, filed on Jun. 27, 2014.

(51) Int. Cl.
| | | |
|---|---|---|
| *C12Q 1/68* | (2018.01) | |
| *C12Q 1/689* | (2018.01) | |
| *G16B 10/00* | (2019.01) | |

(52) U.S. Cl.
CPC ............. *C12Q 1/689* (2013.01); *G16B 10/00* (2019.02)

(58) Field of Classification Search
None
See application file for complete search history.

(56) References Cited

U.S. PATENT DOCUMENTS

2012/0094285 A1*  4/2012  Cangelosi .............. C12Q 1/689
435/6.11

FOREIGN PATENT DOCUMENTS

| EP | 0424473 A1 | 5/1991 |
| WO | WO-2000/008138 A2 | 2/2000 |

OTHER PUBLICATIONS

Menendez et al J Bacteriology. 2002. 184(4): 1078-1088.*
(Continued)

*Primary Examiner* — Carla J Myers
(74) *Attorney, Agent, or Firm* — Marshall, Gerstein & Borun LLP

(57) ABSTRACT

The present disclosure describes a method for identifying a strain or species of bacteria using a single locus sequence typing technique. The single locus useful in the method is the promoter region of the 16S rRNA operon. The method is useful to identify infectious bacteria in a subject, to identifying contaminants in a food source, as well as strain typing and genetic fingerprinting of bacterial families.

11 Claims, 4 Drawing Sheets
Specification includes a Sequence Listing.

(56) References Cited

OTHER PUBLICATIONS

Gonzalez-y-Merchand et al J Bacteriology. Nov. 1997). 179(22): 6949-6958.*

Silcox et al J Clinical Microbiology. 1981. 14(6): 686-691.*

Altschul et al., Basic local alignment search tool, *J. Mol. Biol.*, 215:403-10 (1990).

Bouchet et al., Molecular genetic basis of ribotyping, *Clin. Microbiol. Rev.*, 21(2): 262-73 (2008).

Brusetti et al., Fluorescent-BOX-PCR for resolving bacterial genetic diversity, endemism and biogeography, *BMC Microbiology*, 8:220- (2008).

Coenye et al., Multilocus restriction typing: a novel tool for studying global epidemiology of Burkholderia cepacia complex infection in cystic fibrosis, *J. Infect. Dis.*, 185(10):1454-62 (2002).

Condon et al., Control of rRNA transcription in *Escherichia coli*, *Microbial. Rev.*, 59(4):623-45 (1995).

Feng et al., Progressive sequence alignment as a prerequisite to correct phylogenetic trees, *J. Mol. Evol.*, 35:351-60 (1987).

Hansen et al., Klebsiella typing: pulsed-field gel electrophoresis (PFGE) in comparison with O:K-serotyping, *Clin .Microbiol. Infect.*, 8: 397-404(2002).

Henikoff et al., Amino acid substitution matrices from protein blocks, *Proc. Natl. Acad. Sci. USA*, 89: 10915 (1989).

Karlin et al., Applications and statistics for multiple high-scoring segments in molecular sequences, *Proc. Natl. Acad. Sci. USA*, 90: 5873-87 (1993).

Klappenbach et al., rRNA operon copy number reflects ecological strategies of bacteria, *Appl. Environ. Microbiol.*, 66(4): 1328-33 (2000).

Klappenbach et al., rrndb: the Ribosomal RNA Operon Copy Number Database, *Nucl. Acids Res.* 29: 181-4 (2001).

Kolbert et al., Ribosomal DNA sequencing as a tool for identification of bacterial pathogens, *Curr. Opin. Microbiol.*, 2:299-305 (1999).

Maiden et al., Multilocus sequence typing: a portable approach to the identification of clones within populations of pathogenic microorganisms, *Proc. Natl. Acad. Sci. USA*, 95: 3140-5 (1998).

Needleman et al., A general method applicable to the search for similarities in the amino acid sequence of two proteins, *J. Mol. Biol.*, 48: 443 (1970).

Nemoy et al., Multilocus sequence typing versus pulsed-field gel electrophoresis for characterization of extended-spectrum beta-lactamase-producing *Escherichia coli* isolates, *J. Clin. Microbiol.*, 43(4): 1776-81 (2005).

Pearson et al., Improved tools for biological sequence comparison, *Proc. Natl. Acad. Sci. USA*, 85: 2444 (1988).

Sharp, Fast and sensitive multiple sequence alignments on a microcomputer, *CABIOS*, 5(2):151-3 (1989).

Thompson et al., CLUSTAL W: improving the sensitivity of progressive multiple sequence alignment through sequence weighting, position-specific gap penalties and weight matrix choice, *Nucleic Acids Research*, 22: 4673-80 (1994).

Unemo et al., Review and international recommendation of methods for typing neisseria gonorrhoeae isolates and their implications for improved knowledge of gonococcal epidemiology, treatment, and biology, *Clin. Microbiol. Rev.*, 24: 447-58 (2011).

Vimont et al., Comparison of PFGE and multilocus sequence typing for analysis of Klebsiella pneumoniae isolates, *J. Med. Microbiol.*, 57: 1308-109 (2008).

* cited by examiner

Figure 2

| Genus | Reference Strain | Ribosomal copy number | Predicted copy |
|---|---|---|---|
| Achromobacter | A. xylosoxidans-C54 | 3 | $1^B$ |
| Acidovorax | A. avenae spp. Citrulli-AAC00-1 | 3 | $3^A$ |
| Acinetobacter | A. baumanii-AYE | 6 | $5^{A,B,D}$ |
| Actinobacillus | A. pleuropneumoniae-JL03 | 6 | $6^{A,B,C,D}$ |
| Aeromonas | A. hydrophila-ATCC 7966 | 10 | $3^C$ |
| Aggregatibacter | A. aphrophilus-NJ8700 | 6 | $3^C$ |
| Agrobacterium | A. tumifaciens-C58 | 4 | $3^{B,C}$ (C2) |
| Anaplasma | A. marginale-str. Florida | 1 | $1^B$ |
| Amycolatopsis | A. mediterranei-S699 | 4 | $4^{A,B,D}$ |
| Alcanivorax | A. borkumensis-SK2 | 3 | $1^A$ |
| Alicyclobacillus | A. acidocaldarius-DSM 446 | 6 | $1^{A,C}$ |
| Arcobacter | A. nitrofigilis-DSM 7299 | 4 | $3^{A,B,D}$ |
| Azospirillum | A. lipoferum-4B | 9 | $2^{A,B,D}$ |
| Bacteroides | B. fragilis-NCTC 9343 | 6 | $3^{A,C}$ |
| Bacillus | B. cereus-ATCC 10987 | 12 | $3^{A,B,D}$ |
| Bartonella | B. henselae-Houston-1 | 2 | $1^A$ |
| Bifidobacterium | B. dentium-Bd1 | 4 | $3^{A,B}$ |
| Bordetella | B. bronchiseptica-RB50 | 3 | $1^B$ |
| Borrelia | B. burgdorferi-B31 | 1 | $1^{A,D}$ |
| Brachyspira | B. pilosicoli-B2904 | 1 | $1^B$ |
| Bradyrhizobium | B. japonicum-USDA 110 | 1 | $1^{B,D}$ |
| Brucella | B. suis-1330 | 3 | $2^B$ |
| Buchnera | B. aphidicola-APS | 1 | $1^{A,D}$ |
| Burkholderia | B. cenocepacia-AU1054 | 6 | $2^{A,B,D}$ |
| Campylobacter | C. jejuni-NCTC 11168 | 3 | $2^{A,B,D}$ |
| Ca. Phytoplasma asteris | C. asteris-AYWB | 2 | $1^{A,D}$ |
| Chlamydia | C. trachomitis-434/Bu | $2^\$$ | $1^{A,B,D}$ |
| Chlamydophila | C. pneumonia-AR 39 | 1 | $1^{A,B,D}$ |
| Chlorobaculum | C. tepidum-TLS | 2 | $2^{A,D}$ |
| Chlorobium | C. lumicola-DSM 245 | 2 | $1^{A,D}$ |
| Citrobacter | C. rodentium-ICC168 | 7 | $4^{A,B,C,D}$ |
| Clostridium | C. prefringens-ATCC 13124 | 8 | $8^{A,B}$ |
| Corynebacterium | C. diphtheriae-241 | 5 | $3^{B,C,D}$ |
| Coxiella | C. burnetii-RSA 493 | 1 | $1^A$ |
| Cupriavidus | C. taiwanensis-LMG 19424 | 5 | $3^{A,B}$ |
| Deinococcus | D. radiodurans-R1 | 3 | $1^{A,D}$ |
| Desulfovibrio | D. desulfuricans-ATCC 27774 | $3^\$$ | $1^{B,D}$ |
| Erlichia | E. canis-Jake | 1 | $1^{A,D}$ |
| Enterobacter | E. cloacae- ATCC 13047 | 8 | $1^{A,B,C,D}$ |
| Ensifer (Sinorhizobium) | E. meliloti-1021 | 3 | $1^B$ |
| Enterococcus | E. faecalis-V583 | 4 | $2^{B,C,D}$ |

Figure 2 (cont'd)

| Genus | Reference Strain | Ribosomal copy number | Predicted copy |
|---|---|---|---|
| Erwinia | E. amylovora-ATCC 49946 | 7 | $5^{A, B, D}$ |
| Escherichea | E. coli-UTI89 | 7 | $1^{A, B, C, D}$ |
| Eubacterium | E. rectale-ATCC 33656 | 5 | $2^A$ |
| Flavobacterium | F. branchiophilum-FL-15 | 3 | $1^{A, B, D}$ |
| Geobacillus | G. kaustophilus-HTA426 | 9 | $2^B$ |
| Gluconacetobacter | G. diazotrophicus-PAI 5 | 4 | $4^C$ |
| Gordonia | G. bronchialis-DSM 43247 | 2 | $2^D$ |
| Haemophilus | H. influenza-pittEE | 6 | $4^D$ |
| Helicobacter | H. pylori-J99 | 2 | $2^A$ |
| Herbaspirillum | H. seropedicae-SmR1 | 3 | $2^{B, C}$ |
| Herminiimonas | H. arsenicoxydans-NC 009138 | 2 | $1^B$ |
| Janthinobacterium | Janthinobacterium sp.-Marseille | 2 | $1^B$ |
| Klebsiella | K. pneumonia-MGH 78578 | 8 | $5^{A, B, C, D}$ |
| Lactobacillus | L. acidophilus-NCFM | 4 | $2^{A, B}$ |
| Lactococcus | L. lactis-KF147 | 6 | $6^{B, C}$ |
| Legionella | L. pneumophilia-str. Paris | 3 | $1^{A, B, D}$ |
| Leptospira | L. biflexa-Patoc 1 Paris | 2 | $2^{A, B, D}$ |
| Leuconostoc | L. gasicomitatum-LMG 18811 | 4 | $1^{A, B}$ |
| Listeria | L. monocytogenes-4b F2365 | 6 | $3^{A, B, C}$ |
| Marinobacter | M. adhaerens-HP15 | 3 | $1^{A, D}$ |
| Mesorhizobium | M. loti-MAFF303099 | 2 | $1^{B, C}$ |
| Methylibium | M. petroleiphilum-PM1 | 1 | $1^{B \text{ (rubrivivax)}}$ |
| Methylobacterium | M. extorquens-PA1 | 5 | $4^{B, D}$ |
| Mycobacterium | M. leprae-TN | 1 | $1^{B, D}$ |
| Mycoplasma | M. hyopneumoniae-J | 1 | $1^B$ |
| Neisseria | N. gonorrhoeae-FA 1090 | 4 | $1^B$ |
| Neorickettsia | N. Risticii-Illinois | 1 | $1^B$ |
| Nocardia | N. farcinica-IFM 10152 | 3 | $2^{A, B, D}$ |
| Nocardiopsis | N. alba ATCC BAA-2165 | 5 | $3^{A, B, D}$ |
| Ochrobactrum | O. anthropi-ATCC 49188 | 4 | $1^B$ |
| Paenibacillus | P. polymyxa-E681 | 12 | $1^B$ |
| Pantoea | P. ananatis-LMG 20103 | 6 | $6^{A, B, D}$ |
| Pasturella | P. multocida-Pm70 | 6 | $6^{A, C}$ |
| Prevotella | P. denticola-F0289 | 4 | $3^{A, B, D}$ |
| Prochlorococcus | P. marinus-MIT 9313 | 2 | $2^A$ |
| Propionibacterium | P. acidipropionici-ATCC 4875 | 4 | $2^D$ |
| Pseudomonas | P. aeruginosa-PA7 | 4 | $1^{A, B, D}$ |
| Psychrobacter | P. articus-273-4 | 4 | $1^{A, B}$ |
| Ralstonia | R. solanacearum-GMI1000 | 3 | $1^{A, B, D}$ |
| Rhizobium | R. elti-CFN 42 | 3 | $2^B$ |
| Rhodococcus | R. jostii-RHA1 | 4 | $4^{B, D}$ |
| Rickettsia | R. rickettsii-Iowa | 1 | $1^B$ |

Figure 2 (cont'd)

| Genus | Reference Strain | Ribosomal copy number | Predicted copy |
|---|---|---|---|
| *Rubrivivax* | *R. gelatinosus*-IL144 | 3 | $3^B$ |
| *Salmonella* | *S. enterica* subsp. *typhi*-CT18 | 7 | $5^{A, B, C, D}$ |
| *Serratia* | *S. marcescens*-WW4 | 6 | $1^{A, B, D}$ |
| *Shewanella* | *S. putrefaciens*-CN 32 | 8 | $6^{A, B, C, D}$ |
| *Shigella* | *S. dysenteriae*-Sd197 | 7 | $4^{A, B, C, D}$ |
| *Sphingobium* | *S. chlorophenolicum*-L-1 | 3 | $1^{A, B, D}$ |
| *Sphingomonas* | *S. wittichii*-RW1 | 2 | $1^B$ |
| *Spirochaeta* | *S. coccoides*- DSM 17374 | 3 | $1^{A, B, D}$ |
| *Spiroplasma* | *S. taiwanense*-CT-1 | 1 | 1 |
| *Staphylcoccus* | *S. aureus*-USA300 | 5 | $3^{B, C, D}$ |
| *Stenotrophomonas* | *S. maltophilia*-K279a | 4 | $1^{B, C, D}$ |
| *Streptococcus* | *S. pneumoniae*-D39 | 4 | $4^A$ |
| *Strepomyces* | *S. griseus*-NBRC 13350 | 6 | $6^{A, B, D}$ |
| *Synechococcus* | *S. elongatus*-PCC6301 | 2 | $1^{B \text{ (thermo)}}$ |
| *Thermoanerobacter* | *T. italicus*-Ab9 | 4 | $3^B$ |
| *Thermotoga* | *T. maritime*-MSB8 | 1 | $1^{B, D}$ |
| *Treponema* | *T. pallidum*-SS14 | 2 | $1^A$ |
| *Tistrella* | *T. mobilis*-KA081020-065 | 4 | $2^C$ |
| *Ureaplasma* | *U. parvum*-ATCC 700970 | 2 | $1^C$ |
| *Vibrio* | *V. cholera*-O395 | 8 | $2^{A, C}$ |
| *Xanthomonas* | *X. axonopodis pv.citri*-306 | 2 | $1^{B, D}$ |
| *Xylella* | *X. fastidiosa*-GB514 | 2 | $2^B$ |
| *Yersinia* | *Y. pestis*-Antiqua | 7 | $2^A$ |

[A] Organization of 30S, 50S ribosomal proteins
[B] Alignment of operons
[C] Organization of ribosomal intergenic regions
[D] Analysis of flanking genes of ribosomal operons

SEQUENCE LISTING

```
<160> NUMBER OF SEQ ID NOS: 6

<210> SEQ ID NO 1
<211> LENGTH: 23
<212> TYPE: DNA
<213> ORGANISM: Pseudomonas
<220> FEATURE:
<221> NAME/KEY: misc_feature
<222> LOCATION: (3)..(3)
<223> OTHER INFORMATION: B is G or C
<220> FEATURE:
<221> NAME/KEY: misc_feature
<222> LOCATION: (12)..(12)
<223> OTHER INFORMATION: R is G or A

<400> SEQUENCE: 1
cgbgayatca aratcaagyt ggc                                          23

<210> SEQ ID NO 2
<211> LENGTH: 22
<212> TYPE: DNA
<213> ORGANISM: Pseudomonas

<400> SEQUENCE: 2
gctcgacttg catgtgttag gc                                           22

<210> SEQ ID NO 3
<211> LENGTH: 20
<212> TYPE: DNA
<213> ORGANISM: Pseudomonas aeruginosa
<220> FEATURE:
```

```
<221> NAME/KEY: misc_feature
<222> LOCATION: (6)..(6)
<223> OTHER INFORMATION: R is G or A

<400> SEQUENCE: 3
ctgccrgaga tcgagytgtc                                              20

<210> SEQ ID NO 4
<211> LENGTH: 22
<212> TYPE: DNA
<213> ORGANISM: Pseudomonas aeruginosa

<400> SEQUENCE: 4
gctcgacttg catgtgttag gc                                           22

<210> SEQ ID NO 5
<211> LENGTH: 20
<212> TYPE: DNA
<213> ORGANISM: Burkholderia cepacia

<400> SEQUENCE: 5
tcggtgtgcg tctcggccat                                              20

<210> SEQ ID NO 6
<211> LENGTH: 27
<212> TYPE: DNA
<213> ORGANISM: Burkholderia cepacia

<400> SEQUENCE: 6
cctgacttac tttagtgtga gactctt                                      27
```

METHOD FOR BACTERIAL SPECIES IDENTIFICATION AND STRAIN TYPING

CROSS-REFERENCE TO RELATED APPLICATIONS

The present application claims the priority benefit of U.S. Provisional Patent Application No. 62/018,211, filed Jun. 27, 2014, hereby incorporated by reference in its entirety.

FIELD OF THE INVENTION

The present disclosure relates to a method for determining the species and/or strain of a bacteria using a single locus sequence typing technique. The single locus useful in the method is the promoter region of the 16S rRNA operon. The method is useful to identify infectious bacteria in a subject, to identifying contaminants in a food source, as well as strain typing and genetic fingerprinting of bacterial families.

BACKGROUND OF THE INVENTION

To delineate specific strains at the subspecies level, a variety of bacterial genotyping methods have been developed, including pulsed-field gel electrophoresis (PFGE), random amplified polymorphic DNA (RAPD) sequencing, BOX-A1R-based repetitive extragenic palindromic-PCR (BOX-PCR), multilocus sequence typing (MLST) and ribotyping. Each of these has certain advantages and disadvantages with respect to assessing bacterial clonality.

PFGE is a technique that relies on digestion of the entire bacterial genome by rare-cutting restriction endonucleases followed by separation of the resulting large DNA fragments in an agarose gel subjected to pulsed-field electrophoresis. This method can separate large DNA fragments (of 5 to 10 Mbp) in a size-dependent manner, with relatively few bands to compare (Unemo et al., Clin Microbiol Rev. 24: 447-458, 2011). One advantage of PFGE lies in its high discriminatory power (Hansen et al., Clin Microbiol Infect 8, 397-404, 2002), but PFGE is technically difficult and can result in intralab variability in the absence of careful coordination and planning. PFGE can detect chromosomal rearrangements, caused, for example, by mobile elements in the genome and rapid evolutionary rates. In contrast, MLST is more appropriate for strain phylogeny and large-scale epidemiology (Vimont et al., J Med Microbiol 57:1308-1310, 2008).

PCR-based DNA fingerprinting relies on the principle that the primers bind to specific regions of the DNA, and when this binding occurs in the proper orientation and within an optimum distance, species- or strain-specific amplification products may be generated. Primers such as REP1R-Dt and REP2-Dt, which are derived from the repetitive extragenic palindromic (REP) sequences found primarily in gram-negative bacteria have been used. BOX-PCR is a fingerprinting technique based on the BOX dispersed-repeat motif (e.g., using BOXA1R and BOXA2R primers) that are interspersed throughout the bacterial genome. BOX repeats were first identified in *Streptococcus pneumoniae*, but are present in a number of bacterial species. (see e.g., Brusetti et al., BMC Microbiology 8:220-, 2008).

In MLST analysis, multiple genes (loci), typically internal fragments of chromosomal housekeeping genes, are sequenced to measure genetic relatedness and analyze sequence variation between alleles from many strains (Maiden, et al. Proc. Natl. Acad. Sci. USA 95:3140-3145, 1998). The DNA sequences useful in MLST are generally conserved, slow to evolve, and, ideally, distributed throughout the genome. MLST is able to characterize the sequence type of each isolate and the genetic relatedness of isolates can be presented as a dendrogram constructed by using the matrix of pairwise differences between the allelic profiles of the genes analyzed. MLST has gained increasing popularity during the last 15 years with >80 MLST schemes being developed for bacterial species important in human infection. However, this method is limited by the cost and labor involved in amplifying, sequencing, editing and concatenating multiple housekeeping genes. In certain instances, PFGE has been found to be more reliable a strain predictor than MLST, while in other strains, MLST is more reliable (Nemoy et al., J Clin Microbiol. 43(4):1776-1781, 2005).

Ribotyping has also recently been developed in an effort to better categorize bacteria species and strains. A ribosomal operon generally consists of the three genes encoding the structural rRNA molecules, 16S, 23S, and 5S, cotranscribed as a polycistronic operon. The copy numbers, overall ribosomal operon sizes, nucleotide sequences, and secondary structures of the three rRNA genes are highly conserved within a bacterial species, with the 16S rRNA being the most conserved. Therefore, 16S rRNA gene sequencing has recently become popular for identification and taxonomic classification of bacterial species (Bouchet et al., Clin Microbiol Rev. 21(2): 262-273, 2008; Kolbert, et al., Curr. Opin. Microbiol. 2:299-305, 1999).

Ribotyping is based on restriction endonuclease cleavage of total genomic DNA followed by electrophoretic separation, Southern blot transfer, and hybridization of transferred DNA fragments with a radiolabeled ribosomal operon probe. Only those bands containing a portion of the ribosomal operon are visualized. The number of fragments generated by ribotyping is a reflection of the multiplicity of rRNA operons present in a bacterial species. Copy numbers of rRNA operons have been found to range from 1 (e.g., for *Chlamydia trachomatis*) to 15 (e.g., for *Photobacterium profundum*) (Bouchet et al, supra). The Ribosomal RNA Operon Copy Number Database (rrndb) is an Internet-accessible database containing annotated information on rRNA operon copy number among prokaryotes. Gene redundancy is uncommon in prokaryotic genomes, yet the rRNA genes can vary from one to as many as 15 copies. See *rrndb: the Ribosomal RNA Operon Copy Number Database*, Klappenbach et al., Nucl. Acids Res. 29:181-184, 2001.

While the 16S ribosomal subunit gene (16S rRNA) has been widely used to identify bacteria to the species level, this locus is not universally capable of distinguishing all species in a given genus. Multilocus sequencing analyses, often including a portion of the 16S rRNA gene, can enable species assignment when a single gene does not possess sufficient discriminatory power.

WO 2000/008138 describes an rRNA operon alterable bacterium useful for the selection of antibiotics against pathogenic microorganisms. European Patent EP0424473 describes a method of interrupting the expression of a macromolecular synthesis operon in bacteria comprising the step of binding an antisense oligonucleotide to a single stranded DNA or to a mRNA transcribed from the macromolecular synthesis operon. Klappenbach et al., (Appl Environ Microbiol. 66(4):1328-1333, 2000) discuss that no phenotype has been consistently associated with rRNA gene copy number and discloses that the number of rRNA genes correlates with the rate at which phylogenetically diverse bacteria respond to resource availability.

For each bacterial identification technique previously studied, there seem to be strain specific preferences for which method is more effective at differentiating isolates of a particular bacteria, and no one method emerges as the leading method for characterizing bacterial isolates.

SUMMARY OF THE INVENTION

The present disclosure identifies the utility of sequence analysis of the rRNA promoter for both bacterial species identification and strain-level discrimination, taking advantage of the sequence variation found between promoters of the multiple rRNA operons typically present in bacterial species to identify the promoter that best predicted bacterial phylogeny. It was observed that this promoter provided excellent strain level discrimination thereby providing a rapid, cost effective, portable single locus method for bacterial species identification and strain typing.

In various embodiments, the disclosure provides a single locus sequence typing method for identifying an infectious bacteria in a subject having one or more infectious bacteria the method comprising, a) obtaining a sample containing the infectious bacteria from the subject; b) analyzing a polynucleotide sequence of a promoter region of bacterial 16S rRNA operon in the infectious bacteria; and c) identifying the species and/or strain of infectious bacteria based on the sequence of the 16S rRNA promoter region.

In various embodiments, the method further comprises (d) treating the subject with an antibacterial agent against the infectious bacteria identified.

In various embodiments, the subject is a patient in a hospital and the bacteria is a nosocomial infection.

In one embodiment, the bacteria is a multidrug resistant strain of bacteria. In one embodiment, the bacteria is an animal pathogen. In various embodiments, the animal pathogen has been passed to a human subject. Exemplary zoonotic bacteria include, but are not limited to, *Yersinia pestis*, *Brucella* sp., *Chlamydophila psittaci*, *E. coli* O157:H7, *Cryptosporidium parvum*, *Campylobacter*, and *Salmonella*.

In various embodiments, the sample is selected from the group consisting of whole blood, serum, saliva, sputum, urine, cerebrospinal fluid, stool, amniotic fluid, or tissue sample from skin, muscle, buccal or conjunctival mucosa, placenta, gastrointestinal tract or other organs.

In various embodiments, the disclosure provides a method for identifying a bacteria in a contaminated food source having one or more contaminating bacteria, the method comprising, a) obtaining a sample containing bacteria from the contaminated food source; b) analyzing a polynucleotide sequence of a promoter region of bacterial 16S rRNA operon in the contaminating bacteria; and c) identifying the species and/or strain of contaminating bacteria based on the sequence of the 16S rRNA promoter region.

In one embodiment, contemplated is a method for generating a genetic fingerprint map for bacteria comprising a) analyzing a polynucleotide sequence of a promoter region of bacterial 16S rRNA operon of a known or unknown bacterial strain; and b) classifying the bacteria into a family, genus, species and/or strain of bacteria based on the polynucleotide sequence of the promoter region of the 16S rRNA operon.

In various embodiments, the genetic fingerprint is useful to track patient to patient transmission of an infection. In various embodiments, the genetic fingerprint is useful to determine the source of an outbreak of bacterial infection or epidemic or source of food contamination.

In various embodiments, the analyzing is carried out by DNA sequencing analysis of a copy of the 16S rRNA operon promoter. In certain embodiments, the DNA sequencing involves polymerase chain reaction (PCR) analysis.

In various embodiments, DNA is extracted from the bacterial sample and the DNA sequence analyzed. In various embodiments, the bacterial sample is cultured under conditions for bacterial growth prior to analyzing the promoter sequence. It is contemplated that the DNA can be extracted directly from the bacteria prior to any culture of the bacteria.

In various embodiments, the promoter region comprises a portion of the 16S rDNA and regions upstream of the 16S rDNA. In various embodiments, the promoter region is approximately 250 to 450 nucleotides in length. In various embodiments, the promoter region sequenced product is approximately 600 to 1200 nucleotides in length.

In various embodiments, the identification of the species of bacteria is based on a copy of the promoter having one or more characteristics selected from the group consisting of i) distance of the operon from origin of replication; ii) G/C content of the promoter; iii) an operon consisting of $(a)_{16}S$, $(b)_{16}S$ and 23S or (c) all three ribosomal subunit genes (16S, 23S, and 5S) and is found upstream of a cluster of core 30S and 50S ribosomal subunit genes; and, iv) distinctness of the copy from the remaining ribosomal operons in the genome when 16S, 23S, and 5S are aligned, including alignment of intergenic spacer regions.

In various embodiments, the intergenic spacer regions between the 16S and 23S ribosomal subunit genes are selected from the group consisting of (i) lack of tRNA, (ii) tRNAGlu, tRNAAla, or tRNAIle; (iii) tRNAIle+tRNAAla; and (iv) tRNAAla+tRNAIle. Variations in the intergenic spacer region between 16S operon copies can provide information for identification of the correct promoter copy.

Also contemplated is a single locus sequence typing kit comprising polynucleotide primers specific for a 16S operon promoter region in one or more bacterial species or strains; and instructions for carrying out a single locus sequencing type analysis on a bacterial sample, wherein bacterial DNA from the sample is amplified using the primers and the sequence of the amplified promoter region is compared to a library of bacterial 16S operon promoter regions and the bacteria is identified based on the sequence of the 16S rRNA promoter.

It is also contemplated that the kit described herein comprises collection of data and the collection of data is on a computer-readable storage medium.

In various embodiments, the identification of the bacteria comprises a comparison of the promoter sequence of the isolated species or strain to other 16S promoter sequences using a computer readable storage media having computer-executable instructions. In certain embodiments, the disclosure provides a computer-readable storage medium having computer-executable instructions stored in a memory device to be executed on a processor for implementing a method for identifying an infectious bacteria in a subject having one or more infectious bacteria or for identifying a contaminating bacteria in a food stock, the method comprising analyzing a polynucleotide sequence of a promoter region of bacterial 16S rRNA operon in the bacteria; and identifying the species and/or strain of infectious or contaminating bacteria based on the sequence of the 16S rRNA promoter region. It is understood that the disclosure comprises a tangible computer readable medium including non-transitory computer readable instructions that, when executed at one or more processors of a system, execute a method as disclosed herein for identifying an infectious or contaminating bacteria.

The invention also provides computer-implemented applications. In one such application, the invention relates to an apparatus for determining the sequence of a bacteria in a sample, comprising a processor and a computer readable storage medium having computer executable instructions adapted to be executed on the processor to analyze information for at least one bacteria with respect to at least one promoter in the 16S operon, that is predictive the species and/or strain of bacteria, and generate an output based on the promoter sequence information, wherein the output comprises at least one parameter to identify the bacteria as disclosed herein.

It should be understood that all combinations of features described herein are contemplated, even if the combination of feature is not specifically found in the same sentence or paragraph herein. This includes in particular the use of all markers disclosed herein, alone or in combination, for analysis individually or in haplotypes, in all aspects of the invention as described herein.

BRIEF DESCRIPTION OF THE DRAWINGS

FIG. 2 is a table showing bacteria analyzed for ribosomal promoter typing and parameters disclosed to be relevant for identifying the promoter for species identification.

DETAILED DESCRIPTION

Figure 1:
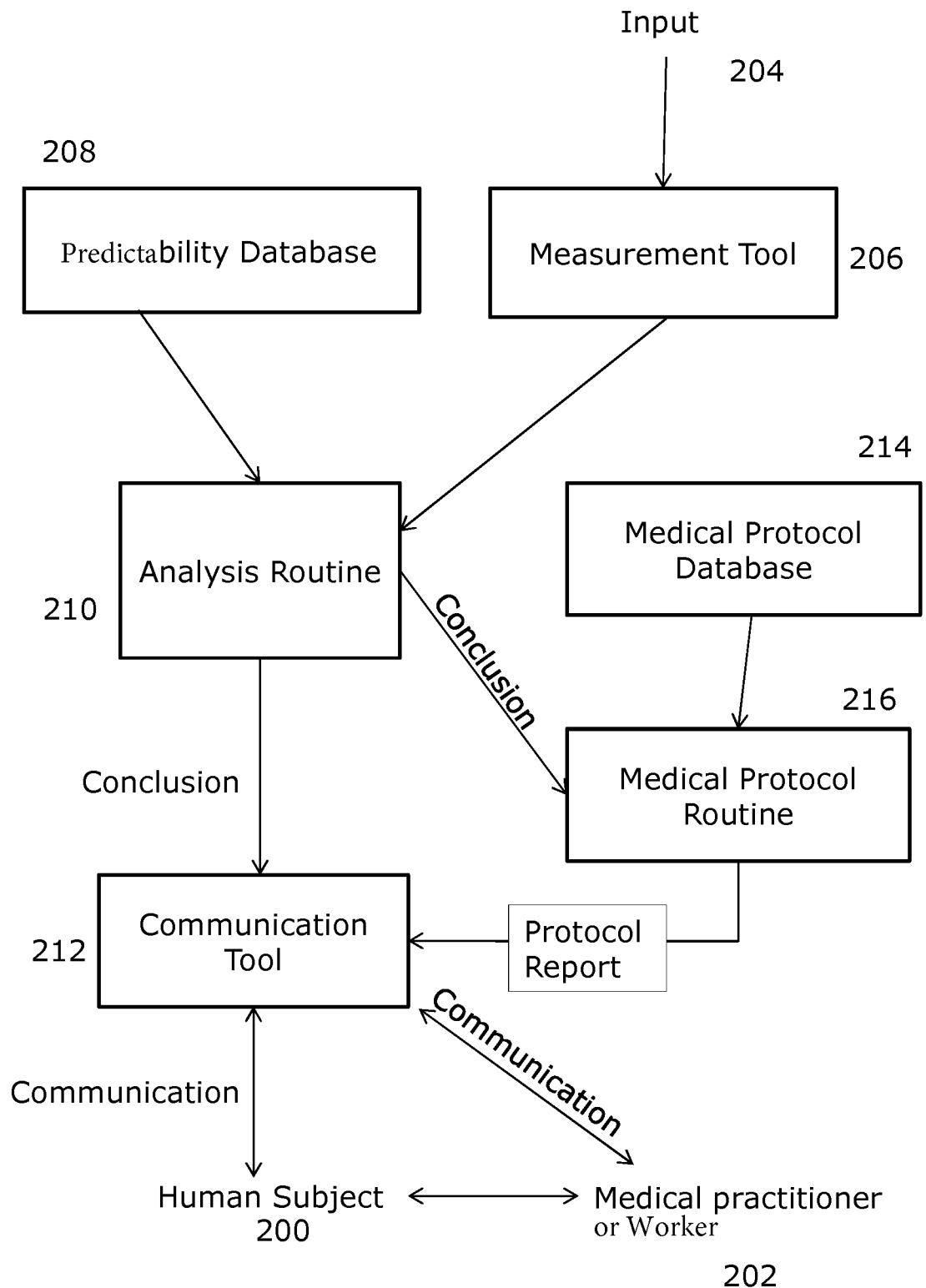
FIG. 1 is a schematic showing an exemplary system for identifying bacteria in a sample as described herein.

The present disclosure is directed to a rapid, cost effective and portable single locus sequence typing (SLST) method to identify and genotype bacteria. This method, which targets a specific ribosomal promoter, can be applied broadly to all bacterial species and predicts phylogenetic relationships that are comparable to those provided by full 16S rRNA gene sequence analysis or multilocus sequence analysis schemes. This approach also provides discriminatory power that is equivalent to multilocus sequence typing schemes in distinguishing clonal and unique strains from epidemiologically related and unrelated strain sets. Using a general set of criteria, the disclosure provides a process to identify which of the multiple ribosomal promoters in a bacterial chromosome should be targeted for this application.

Unless otherwise defined, all technical and scientific terms used herein have the same meaning as commonly understood by one of ordinary skill in the art to which the present disclosure belongs. The following references provide one of skill with a general definition of many of the terms used in this disclosure: Singleton et al., DICTIONARY OF MICROBIOLOGY AND MOLECULAR BIOLOGY (2d Ed. 1994); THE CAMBRIDGE DICTIONARY OF SCIENCE AND TECHNOLOGY (Walker Ed., 1988); THE GLOSSARY OF GENETICS, 5th Ed., R. Rieger et al. (Eds.), Springer Verlag (1991); and Hale & Marham, THE HARPER COLLINS DICTIONARY OF BIOLOGY (1991).

As used in the present disclosure and the appended claims, the terms "a", "an" and "the" include plural reference as well as singular reference unless the context clearly dictates otherwise.

As used herein, the following terms have the meanings ascribed to them unless specified otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3 or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5% or 0.1% of a given value or range. Whenever the term "about" or "approximately" precedes the first numerical value in a series of two or more numerical values, it is understood that the term "about" or "approximately" applies to each one of the numerical values in that series.

A "sample" as described herein, refers to a sample obtained from an individual that contains bacterial nucleic acid (DNA or RNA). Such a sample can be obtained from any source that contains bacterial DNA, including whole blood, serum, saliva, sputum, urine, cerebrospinal fluid, stool, amniotic fluid, or tissue sample from skin, muscle, buccal or conjunctival mucosa, placenta, gastrointestinal tract or other organs.

A "subject" of diagnosis or treatment is a human or non-human animal, including a mammal or a primate. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

A "food source" or "food stock" as used herein refers to any substance containing nutrients, such as carbohydrates, proteins, and fats, that can be ingested by a living organism and metabolized for nourishment. Exemplary food sources that can have bacterial contamination include, meat sources (beef, chicken, pork), fish, vegetables and fruits.

A "contaminating bacteria" or an "infectious bacteria" refers to a bacterial strain or species in a sample which results in detrimental effects to the host comprising the bacteria, or if in a food source, to the subject consuming the food source. A contaminating or infectious bacteria confers undesirable, and potentially harmful, effects in a host. Contaminating or infectious bacteria can be the result of growth of pathogenic or opportunistic bacteria in a subject or food source.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3'-end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence is 5'-TATAC-3' is complementary to a polynucleotide whose sequence is 5'-GTATA-3'. A nucleotide sequence is "substantially complementary" to a reference nucleotide sequence if the sequence complementary to the subject nucleotide sequence is substantially identical to the reference nucleotide sequence.

"Polynucleotide" refers to a polymer composed of nucleotide units. Polynucleotides include naturally occurring nucleic acids, such as deoxyribonucleic acid ("DNA") and ribonucleic acid ("RNA"), as well as nucleic acid analogs. Nucleic acid analogs include those which contain non-naturally occurring bases, nucleotides that engage in linkages with other nucleotides other than the naturally occurring phosphodiester bond, and/or bases attached through linkages other than phosphodiester bonds. Non-limiting examples of nucleotide analogs include phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, e.g., using an automated DNA synthesizer. The term "nucleic acid" typically refers to larger polynucleotides. The term "oligonucleotide" typically refers to shorter polynucleotides. In certain embodiments, an oligonucleotide contains no more than about 50 nucleotides. It will be understood that when a nucleotide sequence is represented by a DNA sequence (i.e., A, T, G, C), this also includes an RNA sequence (i.e., A, U, G, C) in which "U" replaces "T".

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

The term "hybridizing specifically to", "specific hybridization" or "selectively hybridize to" refers to the binding, duplexing, or hybridizing of a nucleic acid molecule preferentially to a particular nucleotide sequence under stringent conditions, e.g., highly stringent conditions, when that sequence is present in a mixture of (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence-dependent, and are different under different environmental parameters. An extensive guide to the hybridization of nucleic acids is found in Tijssen, Laboratory Techniques in Biochemistry and Molecular Biology—Hybridization with Nucleic Acid Probes, Part I, Chapter 2 in "Overview of principles of hybridization and the strategy of nucleic acid probe assays", Elsevier (New York, 1993). In certain embodiments, highly stringent hybridization and wash conditions are about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. In certain embodiments, very stringent conditions are equal to the $T_m$ for a particular probe.

An example of stringent hybridization conditions for hybridization of complementary nucleic acids that have more than 100 complementary residues on a filter in a Southern or Northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see Sambrook et al. for a description of SSC buffer). A high stringency wash can be preceded by a low stringency wash to remove background probe signal. An example of medium stringency wash for a duplex of, e.g., more than 100 nucleotides, is 1×SSC at 45° C. for 15 minutes. An example of low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, Adv. Appl. Math., 2:482 (1981); by the homology alignment algorithm of Needleman and Wunsch, J. Mol. Biol., 48:443 (1970); by the search for similarity method of Pearson and Lipman, Proc. Natl. Acad. Sci. USA, 85:2444 (1988); by computerized implementations of these algorithms (e.g., GAP, BESTFIT, FASTA, and TFASTA in the Wisconsin Genetics Software Package, Genetics Computer Group, Madison, Wis.); or by visual inspection.

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle, J. Mol. Evol., 35:351-360 (1987). The method used is similar to the method described by Higgins and Sharp, CABIOS, 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (see, e.g., Thompson et al., Nucleic Acids Research, 22:4673-4680 (1994)).

Another example of an algorithm that is suitable for determining percent sequence identity and sequence similarity is the BLAST algorithm, which is described in Altschul et al., J. Mol. Biol., 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol., 215:403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, Proc. Natl. Acad. Sci. USA, 89:10915 (1989)).

In addition to calculating percent sequence identity, the BLAST algorithm also performs a statistical analysis of the similarity between two sequences (see, e.g., Karlin and Altschul, Proc. Natl. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. In certain embodiments, a nucleic acid is considered similar to a reference sequence if the smallest sum probability in a comparison of the test nucleic acid to the reference nucleic acid is less than about 0.1, or less than about 0.01, or less than about 0.001.

The terms "treat", "treating" and "treatment" encompass alleviating or abrogating a condition, disorder or disease, or one or more of the symptoms associated with the condition, disorder or disease, and encompass alleviating or eradicating the cause(s) of the condition, disorder or disease itself. In certain embodiments, the terms "treat", "treating", and "treatment" refer to administration of a compound, a pharmaceutical composition or a pharmaceutical dosage form to a subject for the purpose of alleviating, abrogating or preventing a condition, disorder or disease, or symptom(s) associated therewith, or cause(s) thereof. In further embodiments, the term "treatment" refers to prophylactic (preventative) treatment or therapeutic treatment or diagnostic treatment.

The term "effective amount" of a therapeutic means a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health.

A "computer-readable medium" is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

Bacteria

It is contemplated that the methods described herein are useful to study the natural diversity of bacterial species, resolve unclassified isolates into novel species or strains, define regional and global epidemiology of bacterial species, i.e., naturally occurring endemic strains, disease-causing epidemic strains, and strains with the potential to be agents for bioterrorism, study the epidemiology of infectious diseases, differentiate pathogenic organisms, identify bacterial contamination sources (e.g., hospital-acquired/nosocomial, foodborne, animal/zoonosis, environmental), link patient acquisition of a bacterial infection, and track patient-to-patient transmission during infectious disease outbreaks, inform decisions regarding infection prevention and control measures in health care facilities, inform decisions regarding public health response to outbreaks.

Bacteria can be classified on the basis of cell structure, cellular metabolism or on differences in cell components such as DNA, fatty acids, pigments, antigens and quinones. By combining morphology and Gram-staining, most bacteria can be classified as belonging to one of four groups: Gram-positive cocci, Gram-positive bacilli, Gram-negative cocci and Gram-negative bacilli. Bacteria can be aerobic, anaerobic, or facultative anaerobic.

Exemplary bacteria that can be identified using the present methods, include *Acetobacter aurantius, Acinetobacter* species: *Acinetobacter baumannii, Acinetobacter calcoaceticus, Acinetobacter johnsonii, Acinetobacter junii, Acinetobacter lwoffii, Acinetobacter radioresistens, Acinetobacter septicus, Acinetobacter schindleri, Acinetobacter ursingii; Actinomyces* species: *Actinomyces bovis, Actinomyces bowdenii, Actinomyces canis, Actinomyces cardiffensis, Actinomyces catuli, Actinomyces coleocanis, Actinomyces dentalis, Actinomyces denticolens, Actinomyces europaeus, Actinomyces funkei, Actinomyces georgiae, Actinomyces gerencseriae, Actinomyces graevenitzii, Actinomyces hongkongensis, Actinomyces hordeovulneris, Actinomyces howellii, Actinomyces humiferus, Actinomyces hyovaginalis, Actinomyces israelii, Actinomyces marimammalium, Actinomyces meyeri, Actinomyces naeslundii, Actinomyces nasicola, Actinomyces neuii, Actinomyces odontolyticus, Actinomyces oricola, Actinomyces radicidentis, Actinomyces radingae, Actinomyces slackii, Actinomyces streptomycini,*

*Actinomyces suimastitidis, Actinomyces suis, Actinomyces turicensis, Actinomyces urogenitalis, Actinomyces vaccimaxillae, Actinomyces viscosus; Actinobacillus* species: *Actinobacillus actinomycetemcomitans, Actinobacillus arthritidis, Actinobacillus capsulatus, Actinobacillus delphinicola, Actinobacillus equuli, Actinobacillus hominis, Actinobacillus indolicus, Actinobacillus lignieresii, Actinobacillus minor, Actinobacillus muris, Actinobacillus pleuropneumoniae, Actinobacillus porcinus, Actinobacillus rossii, Actinobacillus scotiae, Actinobacillus seminis, Actinobacillus succinogenes, Actinobacillus suis, Actinobacillus ureae; Aeromonas* species: *Aeromonas allosaccharophila, Aeromonas bestiarum, Aeromonas bivalvium, Aeromonas encheleia, Aeromonas enteropelogenes, Aeromonas euchrenophila, Aeromonas hydrophila, Aeromonas ichthiosmia, Aeromonas jandaei, Aeromonas media, Aeromonas molluscorum, Aeromonas popoffii, Aeromonas punctata, Aeromonas salmonicida, Aeromonas schubertii, Aeromonas sharmana, Aeromonas simiae, Aeromonas sobria, Aeromonas veronii; Afipia fells, Agrobacterium* species: *Agrobacterium radiobacter, Agrobacterium rhizogenes, Agrobacterium rubi, Agrobacterium tumefaciens; Agromonas* species, *Alcaligenes* species: *Alcaligenes aquatilis, Alcaligenes eutrophus, Alcaligenes faecalis, Alcaligenes latus, Alcaligenes xylosoxidans; Alishewanella* species, *Alterococcus* species, *Anaplasma phagocytophilum, Anaplasma marginale, Aquamonas* species, *Arcanobacterium haemolyticum, Aranicola* species, *Arsenophonus* species, *Azotivirga* species, *Azotobacter vinelandii, Azotobacter chroococcum*, Bacillary dysentery (Shigellosis), *Bacillus* species: *Bacillus abortus* (*Brucella melitensis* biovar abortus), *Bacillus anthracis* (Anthrax), *Bacillus brevis, Bacillus cereus, Bacillus coagulans, Bacillus fusiformis, Bacillus globigii, Bacillus licheniformis, Bacillus megaterium, Bacillus mycoides, Bacillus natto, Bacillus stearothermophilus, Bacillus subtilis, Bacillus sphaericus, Bacillus thuringiensis; Bacteroides* species: *Bacteroides forsythus* (*Tannerella forsythensis*), *Bacteroides acidifaciens, Bacteroides distasonis* (reclassified as *Parabacteroides distasonis*), *Bacteroides gingivalis, Bacteroides gracilis, Bacteroides fragilis, Bacteroides oris, Bacteroides ovatus, Bacteroides putredinis, Bacteroides pyogenes, Bacteroides stercoris, Bacteroides suis, Bacteroides tectus, Bacteroides thetaiotaomicron, Bacteroides vulgatus, Bartonella* species: *Bartonella alsatica, Bartonella bacilliformis, Bartonella birtlesii, Bartonella bovis, Bartonella capreoli, Bartonella clarridgeiae, Bartonella doshiae, Bartonella elizabethae, Bartonella grahamii, Bartonella henselae* (cat scratch fever), *Bartonella koehlerae, Bartonella muris, Bartonella peromysci, Bartonella quintana, Bartonella rochalimae, Bartonella schoenbuchii, Bartonella talpae, Bartonella taylorii, Bartonella tribocorum, Bartonella vinsonii* spp. *Arupensis, Bartonella vinsonii* spp. *Berkhoffii, Bartonella vinsonii* spp. *Vinsonii, Bartonella washoensis*; BCG (Bacille Calmette-Guerin), *Bergeyella zoohelcum* (*Weeksella zoohelcum*), *Bifidobacterium bifidum, Blastobacter* species, *Blochmannia* species, *Bordetella* species: *Bordetella ansorpii, Bordetella avium, Bordetella bronchiseptica, Bordetella hinzii, Bordetella holmesii, Bordetella parapertussis, Bordetella pertussis* (Whooping cough), *Bordetella petrii, Bordetella trematum; Borrelia* species: *Borrelia burgdorferi, Borrelia afzelii, Borrelia anserina, Borrelia garinii, Borrelia valaisiana, Borrelia hermsii, Borrelia Parkeri, Borrelia recurrentis; Bosea* species, *Bradyrhizobium* species, *Brenneria* species, *Brucella* species: *Brucella abortus, Brucella canis, Brucella melitensis, Brucella neotomae, Brucella ovis, Brucella suis, Brucella pinnipediae; Buchnera* species, *Budvicia* species, *Burkholderia* species: *Burkholderia cepacia* (*Pseudomonas cepacia*), *Burkholderia mallei* (*Pseudomonas mallei/Actinobacillus mallei*), *Burkholderia pseudomallei* (*Pseudomonas pseudomallei*); *Buttiauxella* species, *Calymmatobacterium granulomatis, Campylobacter* species: *Campylobacter coli, Campylobacter concisus, Campylobacter curvus, Campylobacter fetus, Campylobacter gracilis, Campylobacter helveticus, Campylobacter hominis, Campylobacter hyointestinalis, Campylobacter insulaenigrae, Campylobacter jejuni, Campylobacter lanienae, Campylobacter lari, Campylobacter mucosalis, Campylobacter rectus, Campylobacter showae, Campylobacter sputorum, Campylobacter upsaliensis; Capnocytophaga canimorsus* (Dysgonic fermenter type 2), *Corynebacterium* species, *Cardiobacterium hominis, Cedecea* species, *Chlamydia* species: *Chlamydia trachomatis* (*Lymphogranuloma venereum*), *Chlamydia muridarum, Chlamydia suis; Chlamydophila* species: *Chlamydophila pneumoniae, Chlamydophila psittaci* (Psittacosis), *Chlamydophila pecorum, Chlamydophila abortus, Chlamydophila felis, Chlamydophila caviae; Citrobacter* species: *Citrobacter amalonaticus, Citrobacter braakii, Citrobacter farmeri, Citrobacter freundii, Citrobacter gillenii, Citrobacter intermedius, Citrobacter koseri* aka *Citrobacter diversus, Citrobacter murliniae, Citrobacter rodentium, Citrobacter sedlakii, Citrobacter werkmanii, Citrobacter youngae; Clostridium* species: *Clostridium botulinum, Clostridium difficile, Clostridium novyi, Clostridium septicum, Clostridium tetani* (Tetanus), *Clostridium welchii* (*Clostridium perfringens*); *Corynebacterium* species: *Corynebacterium diphtheriae* (Diphtheria), *Corynebacterium amycolatum, Corynebacterium aquaticum, Corynebacterium bovis, Corynebacterium equi, Corynebacterium flavescens, Corynebacterium glutamicum, Corynebacterium haemolyticum, Corynebacterium jeikeiun* (corynebacteria of group JK), *Corynebacterium minutissimum* (Erythrasma), *Corynebacterium parvum* (also called *Propionibacterium* acnes), *Corynebacterium pseudodiptheriticum* (also called *Corynebacterium hofmannii*), *Corynebacterium pseudotuberculosis* (also called *Corynebacterium ovis*), *Corynebacterium pyogenes, Corynebacterium urealyticum* (corynebacteria of group D2), *Corynebacterium renale, Corynebacterium striatum, Corynebacterium tenuis* (*Trichomycosis palmellina, Trichomycosis axillaris*), *Corynebacterium ulcerans, Corynebacterium xerosis; Coxiella burnetii* (Q fever), *Cronobacter* species: *Cronobacter sakazakii, Cronobacter malonaticus, Cronobacter turicensis, Cronobacter muytjensii, Cronobacter dublinensis; Delftia acidovorans* (*Comamonas acidovorans*), *Dickeya* species, *Edwardsiella* species, *Eikenella corrodens, Enterobacter* species: *Enterobacter aerogenes, Enterobacter cloacae, Enterobacter sakazakii; Enterococcus* species: *Enterococcus avium, Enterococcus durans, Enterococcus faecalis* (*Streptococcus faecalis/Streptococcus* Group D), *Enterococcus faecium, Enterococcus solitarius, Enterococcus galllinarum, Enterococcus maloratus; Ehrlichia chaffeensis, Erysipelothrix rhusiopathiae, Erwinia* species, *Escherichia* species: *Escherichia adecarboxylata, Escherichia albertii, Escherichia blattae, Escherichia coli, Escherichia fergusonii, Escherichia hermannii, Escherichia vulneris; Ewingella* species, *Flavobacterium* species: *Flavobacterium aquatile, Flavobacterium branchiophilum, Flavobacterium columnare, Flavobacterium flevense, Flavobacterium gondwanense, Flavobacterium hydatis, Flavobacterium johnsoniae, Flavobacterium pectinovorum, Flavobacterium psychrophilum, Flavobacterium saccharophilum, Flavobacterium salegens, Flavobacterium scophthalmum, Flavobacterium succinans; Francisella* tularensis (Tularaemia), *Francisella novicida*, *Francisella philomiragia*, *Fusobacterium* species: *Fusobacterium necrophorum* (Lemierre syndrome/*Sphaerophorus necrophorus*), *Fusobacterium nucleatum*, *Fusobacterium polymorphum*, *Fusobacterium novum*, *Fusobacterium mortiferum*, *Fusobacterium varium*; *Gardnerella vaginalis*, *Gemella haemolysans*, *Gemella morbillorum* (*Streptococcus morbillorum*), *Grimontella* species, *Haemophilus* species: *Haemophilus aegyptius* (Koch-Weeks *bacillus*), *Haemophilus aphrophilus*, *Haemophilus avium*, *Haemophilus ducreyi* (Chancroid), *Haemophilus felis*, *Haemophilus haemolyticus*, *Haemophilus influenzae* (Pfeiffer *bacillus*), *Haemophilus paracuniculus*, *Haemophilus parahaemolyticus*, *Haemophilus parainfluenzae*, *Haemophilus paraphrophilus* (*Aggregatibacter aphrophilus*), *Haemophilus pertussis*, *Haemophilus pittmaniae*, *Haemophilus somnus*, *Haemophilus vaginalis*; *Hafnia* species, *Hafnia alvei*, *Helicobacter* species: *Helicobacter acinonychis*, *Helicobacter anseris*, *Helicobacter aurati*, *Helicobacter bilis*, *Helicobacter bizzozeronii*, *Helicobacter brantae*, *Helicobacter Canadensis*, *Helicobacter canis*, *Helicobacter cholecystus*, *Helicobacter cinaedi*, *Helicobacter cynogastricus*, *Helicobacter felis*, *Helicobacter fennelliae*, *Helicobacter ganmani*, *Helicobacter heilmannii* (*Gastrospirillum hominis*), *Helicobacter hepaticus*, *Helicobacter mesocricetorum*, *Helicobacter marmotae*, *Helicobacter muridarum*, *Helicobacter mustelae*, *Helicobacter pametensis*, *Helicobacter pullorum*, *Helicobacter pylori* (stomach ulcer), *Helicobacter rappini*, *Helicobacter rodentium*, *Helicobacter salomonis*, *Helicobacter trogontum*, *Helicobacter typhlonius*, *Helicobacter winghamensis*; Human granulocytic ehrlichiosis (*Anaplasma phagocytophilum*/*Ehrlichia phagocytophila*), Human monocytotropic ehrlichiosis (Monocytic ehrlichiosis/*Ehrlichia chaffeensis*), *Klebsiella* species: *Klebsiella granulomatis* (*Calymmatobacterium granulomatis*), *Klebsiella mobilis*, *Klebsiella ornithinolytica*, *Klebsiella oxytoca*, *Klebsiella ozaenae*, *Klebsiella planticola*, *Klebsiella pneumoniae*, *Klebsiella rhinoscleromatis*, *Klebsiella singaporensis*, *Klebsiella terrigena*, *Klebsiella trevisanii*, *Klebsiella variicola*; *Kingella kingae*, *Kluyvera* species, *Lactobacillus* species: *Lactobacillus acetotolerans*, *Lactobacillus acidifarinae*, *Lactobacillus acidipiscis*, *Lactobacillus acidophilus* (Doderlein *bacillus*), *Lactobacillus agilis*, *Lactobacillus algidus*, *Lactobacillus alimentarius*, *Lactobacillus amylolyticus*, *Lactobacillus amylophilus*, *Lactobacillus amylotrophicus*, *Lactobacillus amylovorus*, *Lactobacillus animalis*, *Lactobacillus antri*, *Lactobacillus apodemi*, *Lactobacillus aviarius*, *Lactobacillus bifermentans*, *Lactobacillus brevis*, *Lactobacillus buchneri*, *Lactobacillus camelliae*, *Lactobacillus casei*, *Lactobacillus catenaformis*, *Lactobacillus ceti*, *Lactobacillus coleohominis*, *Lactobacillus collinoides*, *Lactobacillus composti*, *Lactobacillus concavus*, *Lactobacillus coryniformis*, *Lactobacillus crispatus*, *Lactobacillus crustorum*, *Lactobacillus curvatus*, *Lactobacillus delbrueckii*, *Lactobacillus delbrueckii* subsp. *Bulgaricus*, *Lactobacillus delbrueckii* subsp. *Lactis*, *Lactobacillus diolivorans*, *Lactobacillus equi*, *Lactobacillus equigenerosi*, *Lactobacillus farraginis*, *Lactobacillus farciminis*, *Lactobacillus fermentum*, *Lactobacillus formicalis*, *Lactobacillus fructivorans*, *Lactobacillus frumenti*, *Lactobacillus fuchuensis*, *Lactobacillus gallinarum*, *Lactobacillus gasseri*, *Lactobacillus gastricus*, *Lactobacillus ghanensis*, *Lactobacillus graminis*, *Lactobacillus hammesii*, *Lactobacillus hamsteri*, *Lactobacillus harbinensis*, *Lactobacillus hayakitensis*, *Lactobacillus helveticus*, *Lactobacillus hilgardii*, *Lactobacillus homohiochii*, *Lactobacillus iners*, *Lactobacillus ingluviei*, *Lactobacillus intestinalis*, *Lactobacillus jensenii*, *Lactobacillus johnsonii*, *Lactobacillus kalixensis*, *Lactobacillus kefuranofaciens*, *Lactobacillus kefiri*, *Lactobacillus kimchii*, *Lactobacillus kitasatonis*, *Lactobacillus kunkeei*, *Lactobacillus leichmannii*, *Lactobacillus lindneri*, *Lactobacillus malefermentans*, *Lactobacillus mali*, *Lactobacillus manihotivorans*, *Lactobacillus mindensis*, *Lactobacillus mucosae*, *Lactobacillus murinus*, *Lactobacillus nagelii*, *Lactobacillus namurensis*, *Lactobacillus nantensis*, *Lactobacillus oligofermentans*, *Lactobacillus oris*, *Lactobacillus panis*, *Lactobacillus pantheris*, *Lactobacillus parabrevis*, *Lactobacillus parabuchneri*, *Lactobacillus paracollinoides*, *Lactobacillus parafarraginis*, *Lactobacillus parakefiri*, *Lactobacillus paralimentarius*, *Lactobacillus paraplantarum*, *Lactobacillus pentosus*, *Lactobacillus perolens*, *Lactobacillus plantarum*, *Lactobacillus pontis*, *Lactobacillus psittaci*, *Lactobacillus rennini*, *Lactobacillus reuteri*, *Lactobacillus rhamnosus*, *Lactobacillus rimae*, *Lactobacillus rogosae*, *Lactobacillus rossiae*, *Lactobacillus ruminis*, *Lactobacillus saerimneri*, *Lactobacillus sakei*, *Lactobacillus salivarius*, *Lactobacillus sanfranciscensis*, *Lactobacillus satsumensis*, *Lactobacillus secaliphilus*, *Lactobacillus sharpeae*, *Lactobacillus siliginis*, *Lactobacillus spicheri*, *Lactobacillus suebicus*, *Lactobacillus thailandensis*, *Lactobacillus ultunensis*, *Lactobacillus vaccinostercus*, *Lactobacillus vaginalis*, *Lactobacillus versmoldensis*, *Lactobacillus vini*, *Lactobacillus vitulinus*, *Lactobacillus zeae*, *Lactobacillus zymae*; *Leclercia* species, *Legionella* species: *Legionella adelaidensis*, *Legionella anisa*, *Legionella beliardensis*, *Legionella birminghamensis*, *Legionella bozemanii*, *Legionella brunensis*, *Legionella busanensis*, *Legionella cherrii*, *Legionella cincinnatiensis*, *Legionella donaldsonii*, *Legionella drancourtii*, *Legionella drozanskii*, *Legionella erythra*, *Legionella fairfieldensis*, *Legionella fallonii*, *Legionella feeleii*, *Legionella geestiana*, *Legionella* genomospecies, *Legionella gratiana*, *Legionella gresilensis*, *Legionella hackeliae*, *Legionella impletisoli*, *Legionella israelensis*, *Legionella jamestowniensis*, 'Candidatus *Legionella jeonii*', *Legionella jordanis*, *Legionella lansingensis*, *Legionella londiniensis*, *Legionella longbeachae*, *Legionella lytica*, *Legionella maceachernii*, *Legionella micdadei*, *Legionella moravica*, *Legionella nautarum*, *Legionella oakridgensis*, *Legionella parisiensis*, *Legionella pneumophila*, *Legionella quateirensis*, *Legionella quinlivanii*, *Legionella rowbothamii*, *Legionella rubrilucens*, *Legionella sainthelensi*, *Legionella santicrucis*, *Legionella shakespearei*, *Legionella spiritensis*, *Legionella steigerwaltii*, *Legionella taurinensis*, *Legionella tucsonensis*, *Legionella wadsworthii*, *Legionella waltersii*, *Legionella worsleiensis*, *Legionella yabuuchiae*; *Leminorella* species, *Leptospira* species: *Leptospira interrogans*, *Leptospira kirschneri*, *Leptospira noguchii*, *Leptospira alexanderi*, *Leptospira weilii*, *Leptospira* genomospecies 1, *Leptospira borgpetersenii*, *Leptospira santarosai*, *Leptospira inadai*, *Leptospira fainei*, *Leptospira broomii*, *Leptospira licerasiae*, *Leptospira biflexa*, *Leptospira meyeri*, *Leptospira wolbachii*, *Leptospira* genomospecies 3, *Leptospira* genomospecies 4, *Leptospira* genomospecies 5; Lepromatous leprosy (Danielssen-Boeck disease), *Leptospira canicola*, *Leptospira hebdomadis*, Leptospirosis (Weil disease/*Leptospira icterohaemorrhagiae*/*Leptospira interrogans* serovar icterohaemorrhagiae), *Leptotrichia*, *Leuconostoc* species: *Leuconostoc carnosum*, *Leuconostoc citreum*, *Leuconostoc durionis*, *Leuconostoc fallax*, *Leuconostoc ficulneum*, *Leuconostoc fructosum*, *Leuconostoc garlicum*, *Leuconostoc gasicomitatum*, *Leuconostoc gelidum*, *Leuconostoc inhae*, *Leuconostoc kimchii*, *Leuconostoc lactis*, *Leuconostoc mesenteroides*, *Leuconostoc pseudoficulneum*, *Leuconostoc pseudomesenteroides*; *Listeria* species: *Listeria grayi, Listeria innocua, Listeria ivanovii, Listeria monocytogenes* (Listeriosis), *Listeria seeligeri, Listeria welshimeri; Methanobacterium extroquens, Microbacterium multiforme, Micrococcus* species: *Micrococcus antarcticus, Micrococcus flavus, Micrococcus luteus, Micrococcus lylae, Micrococcus mucilaginosis, Micrococcus roseus, Micrococcus sedentarius; Mobiluncus, Moellerella* species, *Morganella* species, *Moraxella* species: *Moraxella atlantae, Moraxella boevrei, Moraxella bovis, Moraxella canis, Moraxella caprae, Moraxella catarrhalis* (*Branhamella catarrhalis*), *Moraxella caviae, Moraxella cuniculi, Moraxella equi, Moraxella lacunata, Moraxella lincolnii, Moraxella nonliquefaciens, Moraxella oblonga, Moraxella osloensis, Moraxella saccharolytica; Morganella morganii, Mycobacterium* species: *Mycobacterium abscessus, Mycobacterium africanum, Mycobacterium agri, Mycobacterium aichiense, Mycobacterium alvei, Mycobacterium arupense, Mycobacterium asiaticum, Mycobacterium aubagnense, Mycobacterium aurum, Mycobacterium austroafricanum, Mycobacterium avium* (Battey disease/Lady Windermere syndrome), *Mycobacterium avium paratuberculosis* (implicated in Crohn's disease in humans and Johne's disease in sheep), *Mycobacterium avium silvaticum, Mycobacterium avium* "*hominissuis*", *Mycobacterium colombiense, Mycobacterium boenickei, Mycobacterium bohemicum, Mycobacterium bolletii, Mycobacterium botniense, Mycobacterium bovis* (*Bovine* tuberculosis), *Mycobacterium branderi, Mycobacterium brisbanense, Mycobacterium brumae, Mycobacterium canariasense, Mycobacterium caprae, Mycobacterium celatum, Mycobacterium chelonae, Mycobacterium chimaera, Mycobacterium chitae, Mycobacterium chlorophenolicum, Mycobacterium chubuense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fluoroanthenivorans, Mycobacterium fortuitum, Mycobacterium fortuitum* subsp. *Acetamidolyticum, Mycobacterium frederiksbergense, Mycobacterium gadium, Mycobacterium gastri, Mycobacterium genavense, Mycobacterium gilvum, Mycobacterium goodii, Mycobacterium gordonae* (*Mycobacterium aquae*), *Mycobacterium haemophilum, Mycobacterium hassiacum, Mycobacterium heckeshornense, Mycobacterium heidelbergense, Mycobacterium hiberniae, Mycobacterium hodleri, Mycobacterium holsaticum, Mycobacterium houstonense, Mycobacterium immunogenum, Mycobacterium interjectum, Mycobacterium intermedium, Mycobacterium intracellulare, Mycobacterium kansasii, Mycobacterium komossense, Mycobacterium kubicae, Mycobacterium kumamotonense, Mycobacterium lacus, Mycobacterium lentiflavum, Mycobacterium leprae* (causes leprosy or Hansen disease/Hanseniasis), *Mycobacterium lepraemurium, Mycobacterium madagascariense, Mycobacterium mageritense, Mycobacterium malmoense, Mycobacterium marinum* (Fish tank granuloma), *Mycobacterium massiliense, Mycobacterium microti, Mycobacterium monacense, Mycobacterium montefiorense, Mycobacterium moriokaense, Mycobacterium mucogenicum, Mycobacterium murale, Mycobacterium nebraskense, Mycobacterium neoaurum, Mycobacterium neworleansense, Mycobacterium nonchromogenicum, Mycobacterium novocastrense, Mycobacterium obuense, Mycobacterium palustre, Mycobacterium parafortuitum, Mycobacterium parascrofulaceum, Mycobacterium parmense, Mycobacterium peregrinum, Mycobacterium phlei, Mycobacterium phocaicum, Mycobacterium pinnipedii, Mycobacterium porcinum, Mycobacterium poriferae, Mycobacterium pseudoshottsii, Mycobacterium pulveris, Mycobacterium psychrotolerans, Mycobacterium pyrenivorans, Mycobacterium rhodesiae, Mycobacterium saskatchewanense, Mycobacterium scrofulaceum, Mycobacterium senegalense, Mycobacterium seoulense, Mycobacterium septicum, Mycobacterium shimoidei, Mycobacterium shottsii, Mycobacterium simiae, Mycobacterium smegmatis, Mycobacterium sphagni, Mycobacterium szulgai, Mycobacterium terrae, Mycobacterium the rmoresistibile, Mycobacterium tokaiense, Mycobacterium triplex, Mycobacterium triviale, Mycobacterium tuberculosis* (major cause of human tuberculosis), *Mycobacterium bovis, Mycobacterium africanum, Mycobacterium canetti, Mycobacterium caprae, Mycobacterium pinnipedii', Mycobacterium tusciae, Mycobacterium ulcerans* (causes Bairnsdale ulcer/Buruli ulcer), *Mycobacterium vaccae, Mycobacterium vanbaalenii, Mycobacterium wolinskyi, Mycobacterium xenopi; Mycoplasma* species: *Mycoplasma fermentans, Mycoplasma genitalium, Mycoplasma hominis, Mycoplasma penetrans, Mycoplasma phocacerebrale, Mycoplasma pneumoniae, Nanukayami* (Seven-day fever/Gikiyami), *Neisseria* species: *Neisseria gonorrhoea* (*Gonococcus/Gonorrhea*), *Neisseria meningiditis* (Meningococcus), *Neisseria sicca, Neisseria cinerea, Neisseria elongata, Neisseria flavescens, Neisseria lactamica, Neisseria mucosa, Neisseria polysaccharea, Neisseria subflava; Nitrobacter* species, *Nocardia* species: *Nocardia asteroides, Nocardia brasiliensis, Nocardia caviae*; Noma (cancrum oris/gangrenous stomatitis), *Obesumbacterium, Oligotropha* species, *Orientia tsutsugamushi* (Scrub typhus), *Oxalobacter formigenes, Pantoea* species: *Pantoea agglomerans, Pantoea ananatis, Pantoea citrea, Pantoea dispersa, Pantoea punctata, Pantoea stewartii, Pantoea terrea; Pasteurella* species: *Pasteurella aerogenes, Pasteurella anatis, Pasteurella avium, Pasteurella bettyae, Pasteurella caballi, Pasteurella canis, Pasteurella dagmatis, Pasteurella gallicida, Pasteurella gallinarum, Pasteurella granulomatis, Pasteurella langaaensis, Pasteurella lymphangitidis, Pasteurella mairii, Pasteurella multocida, Pasteurella pneumotropica, Pasteurella skyensis, Pasteurella stomatis, Pasteurella testudinis, Pasteurella trehalosi, Pasteurella tularensis, Pasteurella ureae, Pasteurella volantium; Pediococcus* species: *Pediococcus acidilactici, Pediococcus cellicola, Pediococcus claussenii, Pediococcus damnosus, Pediococcus dextrinicus, Pediococcus ethanolidurans, Pediococcus inopinatus, Pediococcus parvulus, Pediococcus pentosaceus, Pediococcus stilesii; Peptostreptococcus* species: *Peptostreptococcus anaerobius, Peptostreptococcus asaccharolyticus, Peptostreptococcus harei, Peptostreptococcus hydrogenalis, Peptostreptococcus indoliticus, Peptostreptococcus ivorii, Peptostreptococcus lacrimalis, Peptostreptococcus lactolyticus, Peptostreptococcus magnus, Peptostreptococcus micros, Peptostreptococcus octavius, Peptostreptococcus prevotii, Peptostreptococcus tetradius, Peptostreptococcus vaginalis; Photorhabdus* species, *Photorhizobium* species, *Plesiomonas shigelloides, Porphyromonas gingivalis, Pragia* species, *Prevotella, Propionibacterium* species: *Propionibacterium acnes, Propionibacterium propionicus; Proteus* species: *Proteus mirabilis, Proteus morganii, Proteus penneri, Proteus rettgeri, Proteus vulgaris; Providencia* species: *Providencia friedericiana, Providencia stuartii; Pseudomonas* species: *Pseudomonas aeruginosa, Pseudomonas alcaligenes, Pseudomonas anguilliseptica, Pseudomonas argentinensis, Pseudomonas borbori, Pseudomonas citronellolis, Pseudomonas flavescens, Pseudomonas mendocina,*

*Pseudomonas nitroreducens, Pseudomonas oleovorans, Pseudomonas pseudoalcaligenes, Pseudomonas resinovorans, Pseudomonas straminea, Pseudomonas aurantiaca, Pseudomonas aureofaciens, Pseudomonas chlororaphis, Pseudomonas fragi, Pseudomonas lundensis, Pseudomonas taetrolens, Pseudomonas Antarctica, Pseudomonas azotoformans, Pseudomonas brassicacearum, Pseudomonas brenneri, Pseudomonas cedrina, Pseudomonas corrugate, Pseudomonas fluorescens, Pseudomonas gessardii, Pseudomonas libanensis, Pseudomonas mandelii, Pseudomonas marginalis, Pseudomonas mediterranea, Pseudomonas meridiana, Pseudomonas migulae, Pseudomonas mucidolens, Pseudomonas orientalis, Pseudomonas panacis, Pseudomonas proteolytica, Pseudomonas rhodesiae, Pseudomonas synxantha, Pseudomonas thivervalensis, Pseudomonas tolaasii, Pseudomonas veronii, Pseudomonas denitrificans, Pseudomonas pertucinogena, Pseudomonas cremoricolorata, Pseudomonas fulva, Pseudomonas monteilii, Pseudomonas mosselii, Pseudomonas oryzihabitans, Pseudomonas parafulva, Pseudomonas plecoglossicida, Pseudomonas putida, Pseudomonas balearica, Pseudomonas luteola, Pseudomonas stutzeri, Pseudomonas amygdale, Pseudomonas avellanae, Pseudomonas caricapapayae, Pseudomonas cichorii, Pseudomonas coronafaciens, Pseudomonas ficuserectae, Pseudomonas meliae, Pseudomonas savastanoi, Pseudomonas syringae, Pseudomonas viridiflava, Pseudomonas abietaniphila, Pseudomonas acidophila, Pseudomonas agarici, Pseudomonas alcaliphila, Pseudomonas alkanolytica, Pseudomonas amyloderamosa, Pseudomonas asplenii, Pseudomonas azotifigens, Pseudomonas cannabina, Pseudomonas coenobios, Pseudomonas congelans, Pseudomonas costantinii, Pseudomonas cruciviae, Pseudomonas delhiensis, Pseudomonas excibis, Pseudomonas extremorientalis, Pseudomonas frederiksbergensis, Pseudomonas fuscovaginae, Pseudomonas gelidicola, Pseudomonas grimontii, Pseudomonas indica, Pseudomonas jessenii, Pseudomonas jinjuensis, Pseudomonas kilonensis, Pseudomonas knackmussii, Pseudomonas koreensis, Pseudomonas lini, Pseudomonas lutea, Pseudomonas moraviensis, Pseudomonas otitidis, Pseudomonas pachastrellae, Pseudomonas palleroniana, Pseudomonas papaveris, Pseudomonas peli, Pseudomonas perolens, Pseudomonas poae, Pseudomonas pohangensis, Pseudomonas psychrophila, Pseudomonas psychrotolerans, Pseudomonas rathonis, Pseudomonas reptilivora, Pseudomonas resiniphila, Pseudomonas rhizosphaerae, Pseudomonas rubescens, Pseudomonas salomonii, Pseudomonas segitis, Pseudomonas septica, Pseudomonas simiae, Pseudomonas suis, Pseudomonas thermotolerans, Pseudomonas tremae, Pseudomonas trivialis, Pseudomonas turbinellae, Pseudomonas tuticorinensis, Pseudomonas umsongensis, Pseudomonas vancouverensis, Pseudomonas vranovensis, Pseudomonas xanthomarina; Rahnella* species, *Ralstonia* species: *Ralstonia basilensis, Ralstonia campinensis, Ralstonia eutropha, Ralstonia gilardii, Ralstonia insidiosa, Ralstonia mannitolilytica, Ralstonia metallidurans, Ralstonia paucula, Ralstonia pickettii, Ralstonia respiraculi, Ralstonia solanacearum, Ralstonia syzygii, Ralstonia taiwanensis; Raoultella* species, *Rhodoblastus* species, *Rhodopseudomonas* species, *Rhinoscleroma, Rhizobium radiobacter, Rhodococcus equi, Rickettsia* species: *Rickettsia africae, Rickettsia akari, Rickettsia australis, Rickettsia conorii, Rickettsia felis, Rickettsia japonica, Rickettsia mooseri, Rickettsia prowazekii* (Typhus fever), *Rickettsia rickettsii, Rickettsia siberica, Rickettsia typhi, Rickettsia conorii, Rickettsia africae, Rickettsia psittaci, Rickettsia quintana, Rickettsia rickettsii, Rickettsia trachomae; Rothia dentocariosa, Salmonella* species: *Salmonella arizonae, Salmonella Bongori, Salmonella enterica, Salmonella enteriditis, Salmonella paratyphi, Salmonella typhi* (Typhoid fever), *Salmonella typhimurium, Salmonella salamae, Salmonella arizonae, Salmonella diarizonae, Salmonella houtenae, Salmonella indica; Samsonia* species, *Serratia* species: *Serratia entomophila, Serratia ficaria, Serratia fonticola, Serratia grimesii, Serratia liquefaciens, Serratia marcescens, Serratia odoriferae, Serratia plymuthica, Serratia proteamaculans, Serratia quinivorans, Serratia rubidaea, Serratia ureilytica; Shewanella putrefaciens, Shigella boydii, Shigella dysenteriae, Shigella flexneri, Shigella sonnei, Sodalis* species, *Spirillum* species: *Spirillum minus* rat bite fever, *Staphylococcus* species: *Staphylococcus aureus, Staphylococcus auricularis, Staphylococcus capitis, Staphylococcus caprae, Staphylococcus cohnii, Staphylococcus epidermidis, Staphylococcus felis, Staphylococcus haemolyticus, Staphylococcus hominis, Staphylococcus intermedius, Staphylococcus lugdunensis, Staphylococcus pettenkoferi, Staphylococcus saprophyticus, Staphylococcus schleiferi, Staphylococcus simulans, Staphylococcus vitulus, Staphylococcus warneri, Staphylococcus xylosus; Stenotrophomonas* species: *Stenotrophomonas acidaminiphila, Stenotrophomonas dokdonensis, Stenotrophomonas koreensis, Stenotrophomonas maltophilia, Stenotrophomonas nitritireducens, Stenotrophomonas rhizophila; Streptobacillus* species: *Streptobacillus moniliformis* (Streptobacillary rat bite fever); *Streptococcus* species: *Streptococcus* Group A, *Streptococcus* Group B, *Streptococcus agalactiae, Streptococcus aginosus, Streptococcus avium, Streptococcus bovis, Streptococcus canis, Streptococcus cricetus, Streptococcus faceium, Streptococcus faecalis, Streptococcus ferus, Streptococcus gallinarum, Streptococcus lactis, Streptococcus milleri, Streptococcus mitior, Streptococcus mitis, Streptococcus mutans, Streptococcus oralis, Streptococcus peroris, Streptococcus pneumoniae, Streptococcus pyogenes, Streptococcus ratti, Streptococcus salivarius, Streptococcus sanguinis, Streptococcus sobrinus, Streptococcus parasanguinis, Streptococcus suis, Streptococcus thermophilus, Streptococcus vestibularis, Streptococcus viridans, Streptococcus uberis, Streptococcus zooepidemicus; Tatumella* species, *Trabulsiella* species, *Treponema* species: *Treponema carateum* (Pinta), *Treponema denticola, Treponema endemicum* (Bejel), *Treponema pallidum* (Syphilis), *Treponema pertenue* (Yaws); *Tropheryma whipplei* (Whipple disease), Tuberculoid leprosy, *Ureaplasma urealyticum, Veillonella, Vibrio* species: *Vibrio aerogenes, Vibrio aestuarianus, Vibrio agarivorans, Vibrio albensis, Vibrio alginolyticus, Vibrio brasiliensis, Vibrio calviensis, Vibrio campbellii, Vibrio chagasii, Vibrio cholerae* (Cholera), *Vibrio cincinnatiensis, Vibrio Comma, Vibrio coralliilyticus, Vibrio crassostreae, Vibrio cyclitrophicus, Vibrio diabolicus, Vibrio diazotrophicus, Vibrio ezurae, Vibrio fischeri, Vibrio fluvialis, Vibrio fortis, Vibrio furnissii, Vibrio gallicus, Vibrio gazogenes, Vibrio gigantis, Vibrio halioticoli, Vibrio harveyi, Vibrio hepatarius, Vibrio hispanicus, Vibrio ichthyoenteri, Vibrio kanaloae, Vibrio lentus, Vibrio litoralis, Vibrio logei, Vibrio mediterranei, Vibrio metschnikovii, Vibrio mimicus, Vibrio mytili, Vibrio natriegens, Vibrio navarrensis, Vibrio neonatus, Vibrio neptunius, Vibrio nereis, Vibrio nigripulchritudo, Vibrio ordalii, Vibrio orientalis, Vibrio pacinii, Vibrio parahaemolyticus, Vibrio pectenicida, Vibrio penaeicida, Vibrio pomeroyi, Vibrio ponticus, Vibrio proteolyticus, Vibrio rotiferianus, Vibrio ruber, Vibrio rumoiensis, Vibrio salmonicida, Vibrio scophthalmi, Vibrio splen-*

*didus, Vibrio superstes, Vibrio tapetis, Vibrio tasmaniensis, Vibrio tubiashii, Vibrio vulnificus, Vibrio wodanis, Vibrio xuii; Vogesella indigofera, Wigglesworthia* species, *Wolbachia* species, *Xenorhabdus* species, *Yersinia enterocolitica, Yersinia pestis, Yersinia pseudotuberculosis,* and *Yokenella* species. In various embodiments, the method is used to identify bacteria set out in FIG. 2.

Common foodbourne bacteria include, but are not limited to *Aeromonas hydrophilia, Bacillus cereus, Campylobacter jejuni, Clostridium botulinum, Clostridium perfringens,* enteropathogenic *Escherichinia coli* such as O157:H7 (*E Coli*), *Listeria monocytogenes, Salmonella, Shigella, Staphylococcus aureus, Vibrio* (e.g., parahaemolyticus) and *Yersinia enterocolitica.*

Bacteria may be analyzed and sequenced directly from the sample without culture or may be cultured under appropriate conditions to grow the bacteria for use in the sequencing analysis. In one embodiment, a bacteria from a sample may be cultured in an appropriate media, such as LB media, or a plate containing agar and the appropriate media. The media may also contain additives for bacterial growth, such as glucose or other sugars. The bacteria can be grown in liquid or solid culture overnight at 37° C. Methods for growing bacteria can be found in standard laboratory manuals, such as *Molecular Cloning,* M. Green, and J. Sambrook (Fourth Edition), 2012, Cold Spring Harbor Laboratory Press and Manual of Clinical Microbiology, $10^{th}$ Edition, Ed. J. Versalovic, John Wiley & Sons, Inc.]

Promoter Region

It is contemplated herein that analysis of a single locus, the 16S operon promoter region can be predictive of the species or strain of infectious or contaminating bacteria in a sample. In various embodiments, the promoter region comprises a portion of the 16S rDNA and regions upstream of the 16S rDNA. In one embodiment, the promoter region is approximately 250 to 450 nucleotides in length. It is contemplated that the promoter region is approximately, 250, 275, 300, 325, 350, 375, 400, 425 or 450 base pairs. It is contemplated that upstream nucleotides of from 200-500 base pairs, from 300-400 base pairs, or approximately 200, 250, 300, 350, 400, 450, 500, 550 or 600 base pairs. It is contemplated that the sequenced product is approximately 400-1200 nucleotides in length, or approximately 500-1000, 600-1200, 400-700, 600-800 base pairs or approximately, 400, 450, 500, 550, 600, 650, 700, 750, 800, 850, 900, 950, 1000, 1050 or 1100 base pairs, or any range in between. In various embodiments, the sequenced product is approximately 600-1200 nucleotides in length.

Antibacterial Agent

It is contemplated herein that if a sample from a subject is identified as having an infectious bacteria, the subject can be treated with one or more antibacterial agents. Antibacterial agents include antibiotics, silver salts thereof, organic acids as antimicrobials in food products, e.g. lactic acid, citric acid, acetic acid, and their salts and essential oils. Exemplary antibiotics, include, but are not limited to, Amikacin disulfate salt, Amikacin hydrate, Anisomycin from *Streptomyces griseolus,* Apramycin sulfate salt, Azithromycin, Blasticidine S hydrochloride, Brefeldin A, Brefeldin A from *Penicillium brefeldianum,* Butirosin sulfate salt, Butirosin A from *Bacillus vitellinus,* Chloramphenicol, Chloramphenicol base, Chloramphenicol succinate sodium salt, Chlortetracycline hydrochloride, Chlortetracycline hydrochloride from *Streptomyces aureofaciens,* Clindamycin 2-phosphate, Clindamycin hydrochloride, Clotrimazole, Cycloheximide from microbial, Demeclocycline hydrochloride, Dibekacin sulfate salt, Dihydrostreptomycin sesquisulfate, Dihydrostreptomycin solution, Doxycycline hyclate, Duramycin from *Streptoverticillium cinnamoneus,* Emetine dihydrochloride hydrate), Erythromycin, Erythromycin USP, Erythromycin powder, Erythromycin, Temephos, Erythromycin estolate, Erythromycin ethyl succinate, Erythromycin standard solution, Erythromycin stearate, Fusidic acid sodium salt, G 418 disulfate salt, G 418 disulfate salt powder, G 418 disulfate salt solution liquid, Gentamicin solution liquid, Gentamicin solution, Gentamicin sulfate *Micromonospora purpurea,* Gentamicin sulfate salt, Gentamicin sulfate salt powder USP, Gentamicin-Glutamine solution liquid, Helvolic acid from *Cephalosporium caerulens,* Hygromycin B *Streptomyces hygroscopicus,* Hygromycin B *Streptomyces hygroscopicus* powder, Hygromycin B solution *Streptomyces hygroscopicus,* Josamycin, Josamycin solution, Kanamycin B sulfate salt, Kanamycin disulfate salt from *Streptomyces kanamyceticus,* Kanamycin monosulfate from *Streptomyces kanamyceticus,* Kanamycin monosulfate from *Streptomyces kanamyceticus* powder USP, Kanamycin solution from *Streptomyces kanamyceticus,* Kirromycin from *Streptomyces collinus,* Lincomycin hydrochloride, Lincomycin standard solution, Meclocycline sulfosalicylate salt, Mepartricin, Midecamycin from *Streptomyces mycarofaciens,* Minocycline hydrochloride crystalline, Neomycin solution, Neomycin trisulfate salt hydrate, Neomycin trisulfate salt hydrate powder, Neomycin trisulfate salt hydrate USP powder, Netilmicin sulfate salt, Nitrofurantoin crystalline, Nourseothricin sulfate, Oleandomycin phosphate salt, Oleandomycin triacetate, Oxytetracycline dihydrate, Oxytetracycline hemicalcium salt, Oxytetracycline hydrochloride, Paromomycin sulfate salt, Puromycin dihydrochloride from *Streptomyces alboniger,* Rapamycin from *Streptomyces hygroscopicus,* Ribostamycin sulfate salt, Rifampicin, Rifamycin SV sodium salt, Rosamicin *Micromonospora rosaria,* Sisomicin sulfate salt, Spectinomycin dihydrochloride hydrate, Spectinomycin dihydrochloride hydrate powder, Spectinomycin dihydrochloride pentahydrate, Spiramycin, Spiramycin from *Streptomyces* sp., Spiramycin solution, Streptomycin solution, Streptomycin sulfate salt, Streptomycin sulfate salt powder, Tetracycline, Tetracycline hydrochloride, Tetracycline hydrochloride USP, Tetracycline hydrochloride powder, Thiamphenicol, Thiostrepton from *Streptomyces azureus,* Tobramycin, Tobramycin sulfate salt, Tunicamycin $A_1$ homolog, Tunicamycin $C_2$ homolog, Tunicamycin *Streptomyces* sp., Tylosin solution, Tylosin tartrate, Viomycin sulfate salt, Virginiamycin $M_1$, (S)-(+)-Camptothecin, 10-Deacetylbaccatin III from *Taxus baccata,* 5-Azacytidine, 7-Aminoactinomycin D, 8-Quinolinol crystalline, 8-Quinolinol hemisulfate salt crystalline, 9-Dihydro-13-acetylbaccatin III from *Taxus canadensis,* Aclarubicin, Aclarubicin hydrochloride, Actinomycin D from *Streptomyces* sp., Actinomycin I from *Streptomyces antibioticus,* Actinomycin V from *Streptomyces antibioticus,* Aphidicolin *Nigrospora sphaerica,* Bafilomycin A1 from *Streptomyces griseus,* Bleomycin sulfate from *Streptomyces verticillus,* Capreomycin sulfate from *Streptomyces capreolus,* Chromomycin $A_3$ *Streptomyces griseus,* Cinoxacin, Ciprofloxacin BioChemika, cis-Diammineplatinum(II) dichloride, Coumermycin A1, Cytochalasin B *Helminthosporium dematioideum,* Cytochalasin D *Zygosporium mansonii,* Dacarbazine, Daunorubicin hydrochloride, Daunorubicin hydrochloride USP, Distamycin A hydrochloride from *Streptomyces distallicus,* Doxorubicin hydrochloride, Echinomycin, Echinomycin BioChemika, Enrofloxacin BioChemika, Etoposide, Etoposide solid, Flumequine, Formycin, Fumagillin from *Aspergillus fumigatus,* Ganciclovir, Gliotoxin from *Gliocla-* dium fimbriatum, Lomefloxacin hydrochloride, Metronidazole purum, Mithramycin A from *Streptomyces plicatus*, Mitomycin C *Streptomyces caespitosus*, Nalidixic acid, Nalidixic acid sodium salt, Nalidixic acid sodium salt powder, Netropsin dihydrochloride hydrate, Nitrofurantoin, Nogalamycin from *Streptomyces nogalater*, Nonactin from *Streptomyces tsusimaensis*, Novobiocin sodium salt, Ofloxacin, Oxolinic acid, Paclitaxel from *Taxus yannanensis*, Paclitaxel from *Taxus brevifolia*, Phenazine methosulfate, Phleomycin *Streptomyces verticillus*, Pipemidic acid, Rebeccamycin from *Saccharothrix aerocolonigenes*, Sinefungin, Streptonigrin from *Streptomyces flocculus*, Streptozocin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Trimethoprim, Trimethoprim lactate salt, Tubercidin from *Streptomyces tubercidicus*, 5-Azacytidine, Cordycepin, Formycin A, (+)-6-Aminopenicillanic acid, 7-Aminodesacetoxycephalosporanic acid, Amoxicillin, Ampicillin, Ampicillin sodium salt, Ampicillin trihydrate, Ampicillin trihydrate USP, Azlocillin sodium salt, Bacitracin *Bacillus licheniformis*, Bacitracin zinc salt *Bacillus licheniformis*, Carbenicillin disodium salt, Cefaclor, Cefamandole lithium salt, Cefamandole nafate, Cefamandole sodium salt, Cefazolin sodium salt, Cefinetazole sodium salt, Cefoperazone sodium salt, Cefotaxime sodium salt, Cefsulodin sodium salt, Cefsulodin sodium salt hydrate, Ceftriaxone sodium salt, Cephalexin hydrate, Cephalosporin C zinc salt, Cephalothin sodium salt, Cephapirin sodium salt, Cephradine, Cloxacillin sodium salt, Cloxacillin sodium salt monohydrate, D-Penicillamine hydrochloride, D-Cycloserine microbial, D-Cycloserine powder, Dicloxacillin sodium salt monohydrate, D-Penicillamine, Econazole nitrate salt, Ethambutol dihydrochloride, Lysostaphin from *Staphylococcus staphylolyticus*, Moxalactam sodium salt, Nafcillin sodium salt monohydrate, Nikkomycin, Nikkomycin Z *Streptomyces tendae*, Nitrofurantoin crystalline, Oxacillin sodium salt, Penicillic acid powder, Penicillin G potassium salt, Penicillin G potassium salt powder, Penicillin G potassium salt, Penicillin G sodium salt hydrate powder, Penicillin G sodium salt powder, Penicillin G sodium salt, Phenethicillin potassium salt, Phenoxymethylpenicillinic acid potassium salt, Phosphomycin disodium salt, Pipemidic acid, Piperacillin sodium salt, Ristomycin monosulfate, Vancomycin hydrochloride from *Streptomyces orientalis*, 2-Mercaptopyridine N-oxide sodium salt, 4-Bromocalcimycin A23187 BioChemika, Alamethicin *Trichoderma viride*, Amphotericin B *Streptomyces* sp., Amphotericin B preparation, Calcimycin A23187, Calcimycin A23187 hemi(calcium-magnesium) salt, Calcimycin A23187 hemicalcium salt, Calcimycin A23187 hemimagnesium salt, Chlorhexidine diacetate salt monohydrate, Chlorhexidine diacetate salt hydrate, Chlorhexidine digluconate, Clotrimazole, Colistin sodium methanesulfonate, Colistin sodium methanesulfonate from *Bacillus colistinus*, Colistin sulfate salt, Econazole nitrate salt, Hydrocortisone 21-acetate, Filipin complex *Streptomyces filipinensis*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Ionomycin calcium salt *Streptomyces conglobatus*, Lasalocid A sodium salt, Lonomycin A sodium salt from *Streptomyces ribosidificus*, Monensin sodium salt, N-(6-Aminohexyl)-5-chloro-1-naphthalenesulfonamide hydrochloride, Narasin from *Streptomyces auriofaciens*, Nigericin sodium salt from *Streptomyces hygroscopicus*, Nisin from *Streptococcus lactis*, Nonactin from *Streptomyces* sp., Nystatin, Nystatin powder, Phenazine methosulfate, Pimaricin, Pimaricin from *Streptomyces chattanoogensis*, Polymyxin B solution, Polymyxin B sulfate salt, DL-Penicillamine acetone adduct hydrochloride monohydrate, Polymyxin B sulfate salt powder USP, Praziquantel, Salinomycin from *Streptomyces albus*, Salinomycin from *Streptomyces albus*, Surfactin from *Bacillus subtilis*, Valinomycin, (+)-Usnic acid from *Usnea dasypoga*, (+−)-Miconazole nitrate salt, (S)-(+)-Camptothecin, 1-Deoxymannojirimycin hydrochloride, 1-Deoxynojirimycin hydrochloride, 2-Heptyl-4-hydroxyquinoline N-oxide, Cordycepin, 1,10-Phenanthroline hydrochloride monohydrate puriss., 6-Diazo-5-oxo-L-norleucine, 8-Quinolinol crystalline, 8-Quinolinol hemisulfate salt, Antimycin A from *Streptomyces* sp., Antimycin $A_1$, Antimycin $A_2$, Antimycin $A_3$, Antipain, Ascomycin, Azaserine, Bafilomycin A1 from *Streptomyces griseus*, Bafilomycin B1 from *Streptomyces* species, Cerulenin BioChemika, Chloroquine diphosphate salt, Cinoxacin, Ciprofloxacin, Mevastatin BioChemika, Concanamycin A, Concanamycin A *Streptomyces* sp, Concanamycin C from *Streptomyces* species, Coumermycin A1, Cyclosporin A from *Tolypocladium inflatum*, Cyclosporin A, Econazole nitrate salt, Enrofloxacin, Etoposide, Flumequine, Formycin A, Furazolidone, Fusaric acid from *Gibberella fujikuroi*, Geldanamycin from *Streptomyces hygroscopicus*, Gliotoxin from *Gliocladium fimbriatum*, Gramicidin A from *Bacillus brevis*, Gramicidin C from *Bacillus brevis*, Gramicidin from *Bacillus aneurinolyticus* (*Bacillus brevis*), Gramicidin from *Bacillus brevis*, Herbimycin A from *Streptomyces hygroscopicus*, Indomethacin, Irgasan, Lomefloxacin hydrochloride, Mycophenolic acid powder, Myxothiazol BioChemika, N-(6-Aminohexyl)-5-chloro-1-naphthalenesulfonamide hydrochloride, Nalidixic acid, Netropsin dihydrochloride hydrate, Niclosamide, Nikkomycin BioChemika, Nikkomycin Z *Streptomyces tendae*, N-Methyl-1-deoxynojirimycin, Nogalamycin from *Streptomyces nogalater*, Nonactin .quadrature.80% from *Streptomyces tsusimaensis*, Nonactin from *Streptomyces* sp., Novobiocin sodium salt, Ofloxacin, Oleandomycin triacetate, Oligomycin *Streptomyces* diastatochromogenes, Oligomycin A, Oligomycin B, Oligomycin C, Oligomycin *Streptomyces* diastatochromogenes, Oxolinic acid, Piericidin A from *Streptomyces mobaraensis*, Pipemidic acid, Radicicol from *Diheterospora chlamydosporia* solid, Rapamycin from *Streptomyces hygroscopicus*, Rebeccamycin from *Saccharothrix aerocolonigenes*, Sinefungin, Staurosporine *Streptomyces* sp., Stigmatellin, Succinylsulfathiazole, Sulfadiazine, Sulfadimethoxine, Sulfaguanidine purum, Sulfamethazine, Sulfamonomethoxine, Sulfanilamide, Sulfaquinoxaline sodium salt, Sulfasalazine, Sulfathiazole sodium salt, Triacsin C from *Streptomyces* sp., Trimethoprim, Trimethoprim lactate salt, Vineomycin $A_1$ from *Streptomyces albogriseolus* subsp., Tectorigenin, and Paracelsin *Trichoderma reesei*.

Database

Determining the strain or species of bacteria in a sample can alternatively or additionally comprise comparing nucleic acid sequence data and/or protein sequence data (genotype data) to a database containing correlation data between promoter sequence characteristics described herein and identification of a bacterial strain and/or species. The database can be part of a computer-readable medium described herein.

In a specific aspect of the invention, the database comprises at least one measure of identification of the bacteria in the sample. For example, the database may comprise assessment tools for analyzing G/C content, distance from the origin of replication, etc., associated with particular bacterial strains and species. The database may also encompass use of such assessment tools with particular combinations for multiple such parameters.

In another specific aspect of the invention, the database comprises a look-up table containing at least one of the aforementioned parameters for bacterial identification based on the 16S rDNA promoter sequence.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

An exemplary system of the invention, which may be used to implement one or more steps of methods of the invention, includes a computing device in the form of a computer. Components of computer may include, but are not limited to, a processor, a system memory, a memory/graphics interface, and an I/O interface. The system memory and a graphics processor may be coupled to the memory/graphics interface. A monitor or other graphic output device may be coupled to the graphics processor.

The system memory includes computer storage media in the form of volatile and/or nonvolatile memory such as read only memory (ROM) and random access memory (RAM). The system ROM may contain permanent system data, such as identifying and manufacturing information. In some embodiments, a basic input/output system (BIOS) may also be stored in system ROM. RAM typically contains data and/or program modules that are immediately accessible to and/or presently being operated on by processor.

The computer may also include removable/non-removable, volatile/nonvolatile computer storage media. By way of example only, the system contemplates a hard disk drive that reads from or writes to non-removable, nonvolatile magnetic media. The hard disk drive may be a conventional hard disk drive.

Removable media, such as a universal serial bus (USB) memory, firewire (IEEE 1394), or CD/DVD drive may be connected to the computer directly or through an interface. A storage media may be coupled through interface. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like.

The drives and their associated computer storage media discussed, provide storage of computer readable instructions, data structures, program modules and other data for the computer. For example, a hard disk drive may store an operating system, application programs, other program modules, and program data. A user may enter commands and information into the computer through input devices such as a mouse/keyboard or other input device combination.

The computer may operate in a networked environment using logical connections to one or more remote computers, such as a remote computer via a network interface controller (NIC). The remote computer may be a personal computer, a server, a router, a network PC, a peer device or other common network node, and typically includes many or all of the elements described above relative to the computer. The connection between the NIC 170 and the remote computer may include a local area network (LAN), a wide area network (WAN), or both, but may also include other networks. Such networking environments are commonplace in offices, enterprise-wide computer networks, intranets, and the Internet. The remote computer may also represent a web server supporting interactive sessions with the computer, or in the specific case of location-based applications may be a location server or an application server.

In some embodiments, the network interface may use a modem when a broadband connection is not available or is not used. It will be appreciated that the network connection shown is exemplary and other means of establishing a communications link between the computers may be used.

In some variations, the system includes tools for performing at least one step, preferably two or more steps, and in some aspects all steps of a method of the invention, where the tools are operably linked to each other. Operable linkage describes a linkage through which components can function with each other to perform their purpose.

Referring to FIG. 1, an exemplary system includes a predictability database 208 that is operatively coupled to a computer-readable medium of the system and that contains information correlating the 16S promoter sequence and predictability as to the species and/or strain of bacteria.

In a simple variation, the predictability database 208 contains data relating to the frequency that a particular characteristic described herein has been observed in a population of bacteria. Such data provides an prediction as to the species and/or strain of bacteria. In another variation, the predictability database includes similar data with respect to two or more characteristics, thereby providing a useful reference if the bacteria has any of the analyzed parameters.

In addition to the predictability database 208, the system further includes a measurement tool 206 programmed to receive an input 204 from or about the sample and generate an output that contains information about the promoter sequence. (The input 204 is not part of the system per se but is illustrated in the schematic FIG. 1.) Thus, the input 204 will contain a sample or contain data from which the sequence of the promoter can be directly read, or analytically determined.

In another variation, the input 204 from the sample contains data that is unannotated or insufficiently annotated with respect parameters for predicting the bacterial strain and/or species in the sample. In such variations of the invention, the measurement tool 206 comprises a tool, preferably stored on a computer-readable medium of the system and adapted to be executed on a processor of the system, to receive a data input about a sample and determine information about the promoter sequence. For example, the measurement tool 206 contains instructions, preferably executable on a processor of the system, for analyzing the unannotated input data and determining a characteristic of the promoter sequence sufficient to help in prediction of the bacterial species and/or strain.

In yet another variation, the input 204 from the sample comprises a biological sample, such as a fluid (e.g., blood) or tissue sample that contains genetic material of the bacteria that can be analyzed to determine the promoter sequence. In this variation, an exemplary measurement tool 206 includes laboratory equipment for processing and analyzing the sample to determine the nucleotide sequence or other parameter of the promoter sequence.

In some variations the measurement tool 206 includes: a nucleotide sequencer (e.g., an automated DNA sequencer) that is capable of determining nucleotide sequence information from nucleic acid obtained from or amplified from the biological sample; and an analysis tool stored on a computer-readable medium of the system and adapted to be executed on a processor of the system, to determine the presence or absence of the at least one marker allele based on the nucleotide sequence information.

In some variations, the measurement tool 206 further includes additional equipment and/or chemical reagents for processing the biological sample to purify and/or amplify nucleic acid of the bacteria for further analysis using a sequencer or other analytical equipment.

The exemplary system further includes an analysis tool or routine 210 that: is operatively coupled to the predictability database 204 and operatively coupled to the measurement tool 206, is stored on a computer-readable medium of the system, is adapted to be executed on a processor of the system to compare the information about the sample with the sequence information in the predictive database and generate a conclusion with respect to species and/or strain of bacteria in a sample. In simple terms, the analysis tool looks at the promoter sequence characteristics as described herein by the measurement tool, and compares this information to the predictive database, to determine a species and/or strain of the bacteria. The prediction can be based on a single parameter, or multiple parameters, as described above, that is collected and included as part of the input 204 from the sample, and that also is stored in the predictive database with respect to a population of other bacteria. Generally speaking, each parameter of interest is weighted to provide a conclusion with respect to determination of bacterial species and/or strain. Such a conclusion is expressed in the conclusion in any statistically useful form.

In some variations of the invention, the system as just described further includes a communication tool 212. For example, the communication tool 212 is operatively connected to the analysis routine 210 and comprises a routine stored on a computer-readable medium of the system and adapted to be executed on a processor of the system, to: generate a communication containing the conclusion; and to transmit the communication to a laboratory worker or medical practitioner, and/or enable the worker or medical practitioner to access the communication. In some variations, the communication is provided in a tangible form, such as a printed report or report stored on a computer readable medium such as a flash drive or optical disk. In some variations, the communication is provided electronically with an output that is visible on a video display or audio output (e.g., speaker). In some variations, the communication is transmitted to the worker or the medical practitioner, e.g., electronically or through the mail. In some variations, the system is designed to permit the subject or medical practitioner to access the communication, e.g., by telephone or computer. For instance, the system may include software residing on a memory and executed by a processor of a computer used by the worker or the medical practitioner, with which the subject or practitioner can access the communication, preferably securely, over the internet or other network connection. In some variations of the system, this computer will be located remotely from other components of the system, e.g., at a location of the worker's or medical practitioner's choosing.

In some variations of the invention, the system as described (including embodiments with or without the communication tool) further includes components that add a treatment or prophylaxis utility to the system. For instance, value is added to a determination of bacterial species and/or strain when a medical practitioner can prescribe or administer a standard of care that can reduce bacterial infection, e.g., administration of an antibiotic as described herein.

For example, in some variations, the system further includes a medical protocol database 214 operatively connected to a computer-readable medium of the system and containing information correlating the prediction of the infectious or contaminating bacteria and a protocol for treating the bacterial infection. Such medical protocols include any variety of medicines, or additional diagnostic tests, and the like that are designed to achieve one of the aforementioned goals.

The system of this embodiment further includes a medical protocol tool or routine 216, operatively connected to the medical protocol database 214 and to the analysis tool or routine 210. The medical protocol tool or routine 216 preferably is stored on a computer-readable medium of the system, and adapted to be executed on a processor of the system, to: (i) compare (or correlate) the conclusion that is obtained from the analysis routine 210 and the medical protocol database 214, and (ii) generate a protocol report with respect to the probability that one or more medical protocols in the medical protocol database will achieve one or more of the goals of treating the bacterial infection. The probability can be based on empirical evidence collected from a samples of bacteria and expressed either in absolute terms (e.g., compared to making no intervention), or expressed in relative terms, to highlight the comparative or additive benefits of two or more protocols.

In some variations, a system of the disclosure is a system for identifying a bacterial species or strain, the system comprising:

at least one processor;

at least one computer-readable medium;

a predictive database operatively coupled to a computer-readable medium of the system and containing population information correlating the presence or absence of one or more properties of a 16S promoter operon in a bacteria;

a measurement tool that receives an input about the bacteria and generates information from the input about the sequence of the 16S rRNA promoter indicative of the species and/or strain of bacteria; and an analysis tool that:

is operatively coupled to the predictive database and the measurement tool, is stored on a computer-readable medium of the system, is adapted to be executed on a processor of the system, to compare the information about the bacteria with the promoter sequence information in the predictive database and generate a conclusion with respect to species and/or strain of bacteria in a sample.

Exemplary processors (processing units) include all variety of microprocessors and other processing units used in computing devices. Exemplary computer-readable media are described above. When two or more components of the system involve a processor or a computer-readable medium, the system generally can be created where a single processor and/or computer readable medium is dedicated to a single component of the system; or where two or more functions share a single processor and/or share a single computer readable medium, such that the system contains as few as one processor and/or one computer readable medium. In some variations, it is advantageous to use multiple processors or media, for example, where it is convenient to have components of the system at different locations. For instance, some components of a system may be located at a testing laboratory dedicated to laboratory or data analysis, whereas other components, including components (optional) for supplying input information or obtaining an output communication, may be located at a medical treatment or counseling facility (e.g., doctor's office, health clinic, HMO, pharmacist, geneticist, hospital) and/or at the home or business of the human subject (patient) for whom the testing service is performed.

EXAMPLES

Example 1

Bacterial species often have multiple, non-identical ribosomal operons scattered throughout their genomes. The sequence variation in this operon includes variation in the 16S rRNA gene, despite its widespread use in phylogenetic analyses. For example, three to six variants of the 16S rRNA gene can be found among the 5-6 copies of the ribosomal operon found in *Burkholderia* species. Similarly, the promoters of the multiple ribosomal operons within the genome exhibit sequence variation. Consequently, the use of the ribosomal promoter for phylogenetic analysis will provide varying results depending on which copy is selected.

Genomes.

Annotated genome sequences of several *Burkholderia* and *Pseudomonas* strains in the NCBI genome database (managed by the National Center for Biotechnology Information, U.S. National Library of Medicine) were used. The *Burkholderia* strains included *Burkholderia ambifaria* AMMD, *Burkholderia mallei* ATCC 23344, *Burkholderia pseudomallei* K96243, *Burkholderia multivorans* ATCC 17616, *Burkholderia cenocepacia* AU1054, *B. cenocepacia* HI2424, *B. cenocepacia* J2315, *B. cenocepacia* MCO-3, *Burkholderia phymatum* STM 815, *Burkholderia phytofirmans* PsJM, *Burkholderia contaminans* str. 383, *Burkholderia vietnamiensis* G4, and *Burkholderia xenovorans* LB400. The *Pseudomonas* species included *Pseudomonas aeruginosa* PA01, *P. aeruginosa* PA7, *P. aeruginosa* LESB58, *P. aeruginosa* UCBPP-PA14, *Pseudomonas putida* F1, *P. putida* GB-1, *P. putida* KT2440, *Pseudomonas fluorescens* Pf-5, *P. fluorescens* Pf01, *Pseudomonas mendocinda* ymp, *Pseudomonas stutzeri* A1501, *Pseudomonas syringae* pv. phaseolicola 1448A, *Pseudomonas syringae* pv. syringae B728a and *Pseudomonas syringae* pv. tomato str. DC3000.

Bacteria.

Strains used in this study were obtained from referring laboratories by the *Burkholderia cepacia* Research Laboratory and Repository.

Ribosomal Promoter and 16S rDNA.

Ribosomal promoter elements were identified as the start of the UP element to the start of mature 16s rDNA (~450 bp) (Condon et al., Microbiol Rev. 59(4):623-45, 1995). For primer design, 200 bp of 16s rDNA and approximately 400 bp upstream was included to capture all possible promoter elements and the upstream gene to design specific primer to a particular promoter. The total DNA sequence length used for *Burkholderia cepacia* complex and *Pseudomonas aeruginosa* was 1,100 bp per promoter. Complete 16S ribosomal sequences were used and based on annotated data using EditSeq software (DNASTAR Inc., Madison, Wis.)

DNA Preparation.

DNA was prepared from bacteria as described previously (Coenye and Lipuma, J Infect Dis. 185(10):1454-62, 2002). In brief, a single CFU was suspended in 20 µl of lysis buffer containing 0.25% (vol/vol) sodium dodecyl sulfate and 0.05 N NaOH. After heating for 15 minutes at 95° C., 180 µl of high-performance liquid chromatography-grade $H_2O$ (Fisher) was added. The suspension was centrifuged at 13,300 rpm for 5 minutes, and the supernatant was stored at 4° C.

Primer Design.

The ribosomal promoter copy of interest was aligned to the corresponding copy from other genomes and were aligned using Clustal V with MegAlign software package (DNASTAR Inc., Madison, Wis.). Primers were manually designed based on conserved regions of DNA. Primers were checked for loops, self-dimers and primer dimers using PrimerSelect software package (DNASTAR Inc., Madison, Wis.). Primers used in this study are listed in Table 1.

TABLE 1

| Species | Annealing Temperature ° C. |
|---|---|
| *Pseudomonas* genus<br>F-CGBGAYATCAARATCAAGYTGGC<br>(SEQ ID NO: 1)<br>R-GCTCGACTTGCATGTGTTAGGC<br>(SEQ ID NO: 2) | 57 |
| *Pseudomonas aeruginosa*<br>F-CTGCCRGAGATCGAGYTGTC<br>(SEQ ID NO: 3)<br>R-GCTCGACTTGCATGTGTTAGGC<br>(SEQ ID NO: 4) | 58 |
| *Burkholderia cepacia* complex<br>F-TCGGTGTGCGTCTCGGCCAT<br>(SEQ ID NO: 5)<br>R-CCTGACTTACTTTAGTGTGAGACTC<br>TT(SEQ ID NO: 6) | 57 |

PCR.

Amplification of targeted DNA was carried out in 25-µl reaction volumes, each containing 2 mM $MgCl_2$, 200 mM Tris-HCL, 500 mM KCl (pH 8.4; Invitrogen, Carlsbad, Calif.), 250 µM (each) deoxynucleoside triphosphates (Bio- Express, Kaysville, Utah), 0.4 µM (each) primer (IDT, Coralville, Iowa), 1 U of Taq polymerase (Invitrogen, Carlsbad, Calif.), and 2 µl of whole-cell bacterial lysate, and adjusted to 25 µl by the addition of high-performance liquid chromatography-grade H$_2$O. Amplification was carried out in a PTC-100 thermocontroller (Bio-Rad, Hercules, Calif.). After an initial denaturization for 2 minutes at 95° C., 30 cycles were completed, each consisting of 30 seconds at 94° C., 30 seconds at the appropriate annealing temperature (Table 1), and 60 seconds at 72° C. A final extension of 5 minutes at 72° C. was applied with an infinite hold at 8° C.

Sequencing of Ribosomal Promoter DNA.

Amplified PCR products were purified using the Qiagen QIAquick PCR purification kit (Qiagen Inc., Valencia, Calif.) following the manufacturer's instructions. DNA sequencing was carried out with an Applied Biosystems ABI model 3730 sequencer using the protocols provided by the manufacturer (PE Applied Biosystems, Foster City, Calif.) by using the BIGDYE® Terminator cycle sequencing ready reaction kit. Sequence chromatograms were visualized and edited with Chromas version 2.31 (Technelysium Pty. Ltd.). All sequences were aligned using MEGALIGN™ (DNAStar); trimmed sequences were saved individually.

Results

Identification of Ribosomal Promoter of Interest.

In our analysis of several dozen species, it was noted that selection of the most appropriate ribosomal operon promoter for predicting phylogenetic relationships follows one of several possible criteria.

Ribosomal operon copy numbers are based on distance from the origin of replication (of the primary chromosome in species with multiple chromosomes). The exceptions are *Chlamydia*, which is based on the position of one of two dnaA copies at positions 624,880 bp-626,247 bp, and *Desulfovibrio*, which is based on the position of one of two dnaA copies at positions 5,316 bp-7,721 bp.

The present studies have shown that the ribosomal operon of interest is located closer to the origin of replication than other ribosomal operons. This operon is commonly adjacent to rpmG (L33) and ribonuclease P, but transcribed and in the opposite direction.

The present analysis has shown that the operon of interest consists of all three ribosomal subunit genes (16S, 23S, and 5S) and is most often found upstream of a cluster of core 30S and 50S ribosomal subunit genes, beginning with rplK (L11) and ending with rplQ (L17). The number of additional 30S and 50S genes in the genome and their proximity to each other decrease with increasing distance from the ribosomal operon of interest.

Additionally, the results indicate the operon of interest is distinct from the remaining ribosomal operons in the genome when these are aligned. This includes all intergenic spacer regions. The intergenic spacer region between the 16S and 23S ribosomal subunit genes includes (i) no tRNA, (ii) tRNA$^{Glu}$, tRNA$^{Ala}$, or tRNA$^{Ile}$ or (iii) tRNA$^{Ile}$+tRNA$^{Ala}$ or tRNA$^{Ala}$+tRNA$^{Ile}$.

Within a genus, there is greater inter-species consistency in the genes flanking the ribosomal operon of interest than there are in genes flanking other ribosomal operons.

Numerous modifications and variations in the invention as set forth in the above illustrative examples are expected to occur to those skilled in the art. Consequently only such limitations as appear in the appended claims should be placed on the invention.

All publications and patent documents cited in this application are incorporated by reference in their entirety to the same extent as if the contents of each individual publication or patent document were incorporated herein.

What is claimed:

1. A single locus sequence typing method for identifying an infectious bacteria strain in a subject having one or more infectious bacteria the method comprising,
   a) obtaining a sample containing the infectious bacteria from the subject;
   b) analyzing polynucleotide sequences of one or more promoter region copies of a bacterial ribosomal RNA rRNA operon; consisting of 16S, 23S and 5S subunit ribosomal RNA, found in the infectious bacteria in the sample,
   wherein the promoter region is approximately 250 to 450 nucleotides in length and wherein the analyzed promoter region polynucleotide sequenced product is approximately 600-1200 nucleotides in length;
   wherein the analysis identifies a selected promoter region sequence copy as predictive of bacterial strain identity based on a characteristic of
   distinctness of the selected promoter region copy sequence from the remaining ribosomal operon sequences in the genome when the 16S subunit promoter sequences are aligned, including alignment of intergenic spacer regions;
   c) identifying the strain of infectious bacteria based on the unique nucleotide sequence of the selected rRNA promoter region by comparison of the selected promoter sequence of the infectious bacteria in (b) to other known rRNA promoter sequences using a computer readable storage media having computer-executable instructions, and
   (d) treating the subject with an antibacterial agent against the infectious bacteria strain identified.

2. The method of claim 1, wherein the subject is a patient in a hospital and the bacteria is a nosocomial infection.

3. The method of claim 1, wherein the bacteria is a multidrug resistant strain of bacteria.

4. The method of claim 1, wherein the bacteria is an animal pathogen.

5. The method of claim 4, wherein the animal pathogen has been passed to a human subject.

6. The method of claim 1, wherein the sample is selected from the group consisting of whole blood, serum, saliva, sputum, urine, cerebrospinal fluid, stool, amniotic fluid, or tissue sample.

7. The method of claim 1, wherein the analyzing is carried out by DNA sequencing analysis of a copy of the rRNA operon promoter.

8. The method of claim 1, wherein the bacterial sample is cultured under conditions for bacterial growth prior to analyzing the promoter sequence.

9. The method of claim 1, wherein DNA is extracted from the bacterial sample and the DNA sequence analyzed.

10. The method of claim 1, wherein the analyzed promoter regions are amplified by polymerase chain reaction and comprise a portion of the 16S rDNA and regions upstream of the 16S rDNA.

11. The method of claim 1, wherein the intergenic spacer regions between the 16S and 23S ribosomal subunit genes are selected from the group consisting of any of the following possible combinations contained within the intergenic space of 16S and 23S rRNA
   (i) lack of tRNA,
   (ii) tRNAGlu, tRNAAla, or tRNAIle;
   (iii) tRNAIle+tRNAAla; and
   (iv) tRNAAla+tRNAIle.

* * * * *

UNITED STATES PATENT AND TRADEMARK OFFICE
CERTIFICATE OF CORRECTION

PATENT NO.           : 10,400,291 B2
APPLICATION NO.      : 14/752391
DATED                : September 3, 2019
INVENTOR(S)          : John LiPuma et al.

Page 1 of 1

It is certified that error appears in the above-identified patent and that said Letters Patent is hereby corrected as shown below:

In the Claims

Column 31, Line 38, Claim 1 "comprising," should read -- comprising: --.

Column 31, Line 63, Claim 1 "(d)" should read -- d) --.

Signed and Sealed this
Twenty-eighth Day of July, 2020

Andrei Iancu
*Director of the United States Patent and Trademark Office*